(12) United States Patent
Cook et al.

(10) Patent No.: US 8,119,781 B2
(45) Date of Patent: *Feb. 21, 2012

(54) LUMINESCENT METAL ION COMPLEXES

(75) Inventors: Ronald M. Cook, Novato, CA (US); Matt Lyttle, San Rafael, CA (US); Mary Katherine Johannson, El Cerrito, CA (US)

(73) Assignee: Biosearch Technologies, Inc., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/644,002

(22) Filed: Dec. 21, 2009

(65) Prior Publication Data

US 2010/0130733 A1 May 27, 2010

Related U.S. Application Data

(63) Continuation of application No. 10/690,806, filed on Oct. 21, 2003, now Pat. No. 7,635,762.

(60) Provisional application No. 60/420,485, filed on Oct. 21, 2002.

(51) Int. Cl.
*C07H 19/00* (2006.01)
*C07H 21/00* (2006.01)

(52) U.S. Cl. .................. 536/22.1; 536/17.1; 536/18.5; 536/18.6

(58) Field of Classification Search .................. None
See application file for complete search history.

(56) References Cited

U.S. PATENT DOCUMENTS 5,998,594 A 12/1999 Goodman et al.

OTHER PUBLICATIONS

Khan et al., "Automated Solid Phase Synthesis of Site-Specifically Labeled Uthenium-Oligonucleotides," Inorg. Chem., 38:418-419 (1999).
Khan et al., "Automated Solid Phase DNA Synthesis and Photophysical Properties of Oligonucleotides Labeled at the 5'-Terminus with $Ru(bpy)_3^{2+}$," Inorg. Chem., 38:3922-3925 (1999).
Hurley et al., "Ru(II) and Os(II) Nucleosides and Oligonucleotides: Synthesis and Properties," *J. Am. Chem. Soc.* 2002, 124 (14), 3749-3762.

*Primary Examiner* — Patrick Lewis
(74) *Attorney, Agent, or Firm* — Morgan, Lewis & Bockius LLP

(57) ABSTRACT

The present invention provides luminescent metal ion complexes for use in a wide range of biological and chemical studies. The luminescent metal ion complexes of the invention comprise a metal ion chelating component covalently bound to a carrier molecule. Also provided are methods of making and using the luminescent metal ion complexes.

38 Claims, 7 Drawing Sheets

LUMINESCENT METAL ION COMPLEXES

CROSS REFERENCE TO RELATED APPLICATIONS

This application is a continuation of U.S. patent application Ser. No. 10/690,806 filed Oct. 21, 2003 and claims priority under 35 U.S.C. §119(e) to U.S. Provisional Patent Application No. 60/,420,485, filed on Oct. 21, 2002, which are incorporated herein by reference in their entirety for all purposes.

BACKGROUND OF THE INVENTION

There is a continuous and expanding need for rapid, highly specific methods of detecting and quantifying chemical, biochemical and biological substances. Of particular value are methods for measuring small quantities of pharmaceuticals, metabolites, microorganisms and other materials of diagnostic value. Examples of such materials include narcotics and poisons, drugs administered for therapeutic purposes, hormones, pathogenic microorganisms and viruses, antibodies, enzymes and nucleic acids.

The presence of a particular analyte can often be determined by binding methods which exploit the high degree of specificity which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the interacting materials. The specific labeling method chosen often dictates the usefulness and versatility of a particular system for detecting a material of interest. A preferred label should be inexpensive, safe, and capable of being attached efficiently to a wide variety of chemical, biochemical, and biological materials without changing the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations. Radioactive labels are, however, expensive, hazardous, and their use requires sophisticated equipment and trained personnel.

Another means of label detection is electrochemiluminescence, voltage is applied to an electrode, triggering a cyclical oxidation-reduction reaction of a metallo-complex resulting in the generation of light. Because no exciting light is used and only the excited state of the metal ion-ligand complex is produced, the background luminescence is very low.

Electrochemical detection of labels has also generated considerable interest due to its high sensitivity. For example, DNA hybridization has been successfully detected electrochemically using an electrochemical mediator to extract electrons from guanine residues in DNA or RNA and carry them to the electrode, where the mediator is regenerated and can participate in additional electron-transfer events (Ontko et al., Inorg. Chem. 38: 1842-1846 (1999)).

Labels that are detectable using fluorescence spectroscopy are of particular interest, because they are safer than radioactive labels and there is a large number of such labels that are known in the art. However, many fluorescent labels suffer from a number of shortcomings, including a small Stokes shift (absorption and emission curves overlap), a lack of photostability, a decrease in emission due to self-quenching, and the requirement of long excitation wavelengths to get near-IR emission. Thus, there is wide interest in photostable fluorescent labels with a large Stokes shift, that are not self quenching, have long fluorescent lifetimes, and have useful redox properties.

Considerable interest has been sparked by luminescent metal ion complex labels that are photostable, have a large Stokes shift, are not self quenching, have long fluorescent times, and have useful redox properties. Luminescent metal ion complex probes have employed metal ions such as ruthenium (Ru), osmonium (Os) and rhenium (Re). Ruthenium has been the most widely studied metal ion for use in luminescent metal ion complex probes. Ruthenium is a transition metal typically in the +2 oxidation state when forming transition metal complexes. Ru-complexes are octahedral with 6 coordination sites. Ruthenium trisbipyridyl ($Ru(bpy)_3$) has been widely studied by photochemists the last 40 years for such applications as solar cells and artificial photosynthesis.

The absorption spectra of ruthenium complexes are a result of several types of transitions: metal centered, ligand centered, and metal-to-ligand charge transfer at around 450 nm. Emission of $Ru(bpy)_3$ is at ca. 650 nm and the lifetime is ca. 1 μs. Ruthenium complexes are normally very stable and the ligand-metal bonds are covalent in character. As a result, the absorption and emission spectra are very sensitive to changes in the ligands. Moreover, the redox chemistry of ruthenium complexes is well known and often reversible between $Ru^{+1}$, $Ru^{+2}$ and $Ru^{+3}$ states.

There is a growing demand for biological and chemical probes with ruthenium complex labels. Due to the many useful properties of Ru-complexes (long lifetime, Stokes-shifted emission, electrochemistry, intercalation), several types of assays are possible with various detection strategies. For example, Ru-complexes may be used in anisotropy, electrochemiluminescence (e.g. the ORIGEN system from IGEN, Inc.), molecular light switching (see, e.g., Ossipov et al., JACS, 123: 3551-3562 (2001)), electrochemical intermolecular studies (Tierney et al., J. Phys. Chem. B, 104: 7574-7576 (2001)), electrochemical detection (H. H. Thorp, Trends in Biotechnology 16: 117-121 (1998)) and well known luminescence detection methods such as time-resolved fluorescence and fluorescence polarization.

Accordingly, strategies have been developed and are currently being sought to label biomolecules (e.g., oligonucleotides and peptides) with Ru-complexes. For example, Ru chelate active esters are commercially available and have been used to post synthetically label oligonucleotides. However, this labeling requires a 5-10 fold stoichiometric excess of the $Ru(bpy)_3$-active ester labeling reagent and has many inherent disadvantages, including laborious separation of the labeling reagent from both the labeled and unlabeled oligonucleotides.

Another method involves the use of a nucleoside phosphoramidite comprising a Ru-complex (Khan et al., Inorg. Chem., 38: 3922-3925 (1999)). The method incorporates the phosphoramidite comprising a Ru-complex into an oligonucleotide using solid phase synthesis protocols. However, these methods do not allow the metal complex label to be incorporated on the 3' end of the oligonucleotide. In addition, the efficiency for coupling the phosphoramidite Ru-complex to the oligonucleotide is poor.

In yet another method, the Ru-complex is added to a nucleic acid after deprotection of the base and cleavage from the solid support. (Tor et al., *JACS*, 124: 3749-3762 (2002)). However, this method exposes ruthenium coordination sites, such as the N7 guanine, which may result in non-specific binding of the ruthenium.

Thus, there is a need in the art for a more efficient method of making luminescent metal ion complexes. The present invention fills these and other needs in the art.

BRIEF SUMMARY OF THE INVENTION

The present invention provides compositions and methods of making a new class of versatile and cost effective luminescent metal ion complexes and components thereof for use in a wide range of applications. The luminescent metal ion complexes are useful in detection and isolation of target analytes such as biomolecules. For greater ease in isolation and detection, the current invention provides both solid phase luminescent metal ion complexes and solution phase luminescent metal ion complexes. In addition, the present invention provides methods of using the probes in assaying, detecting and isolating target analytes. Finally, the present invention provides methods for making and using dual labeled probes, wherein the probes comprise a luminescent metal ion complex and a second label, such as a quencher of excited energy state.

In a first aspect, the invention provides a metal ion coordinating component of a luminescent metal ion complex including:
 (i) a nucleobase comprising a nitrogenous base;
 (ii) a linker covalently bonded to the nitrogenous base; and
 (iii) a metal ion coordinating moiety covalently bonded to the linker to form the metal ion coordinating component of the luminescent metal ion complex.

In another aspect, the invention provides a luminescent metal ion complex between a metal ion and a first metal ion coordinating component, a second metal ion coordinating component and a third metal ion coordinating component. The first metal ion coordinating component of the luminescent metal ion complex includes:
 (i) a nucleobase comprising a nitrogenous base;
 (ii) a linker covalently bonded to the nitrogenous base; and
 (iii) a first metal ion coordinating moiety covalently bonded to the linker.

In another aspect, the invention provides a method of making a nucleic acid probe comprising the step of covalently bonding a first nucleobase to a non-nucleic acid spacer to form the probe, wherein:
 (i) the first nucleobase comprises a nitrogenous base;
 (ii) the nitrogenous base comprises a linker covalently bonded to a first metal ion coordinating moiety; and
 (iii) the non-nucleic acid spacer is covalently bonded a solid support.

In another aspect, the invention provides a method of making a luminescent metal ion complex comprising the step of adding a metal ion to a metal ion coordinating component of a luminescent metal ion complex attached to a solid support.

In another aspect, the present invention provides a method of making a nucleic acid probe comprising a metal ion coordinating component of a luminescent metal ion complex, the method comprising a step wherein a first nucleobase is covalently bonded to a second nucleobase to form the nucleic acid probe, wherein:
 (i) the first nucleobase comprises a nitrogenous base;
 (ii) the nitrogenous base comprises a linker covalently bonded to a first metal ion coordinating moiety; and
 (iii) the non-nucleic acid spacer is covalently bonded to a solid support.

In another aspect, the present invention also provides a family of nucleic probes comprising a metal ion coordinating component covalently attached to a detector oligonucleotide. The luminescent metal ion complex and/or metal ion coordinating components further comprise at least one second label, such as a quencher of excited energy state.

In another aspect, the nucleic acid probe is a dual labeled probe having the structure:

Q-Z—U 

In the formula above, Q represents a quencher moiety. Z is a member selected from a bond and a carrier molecule. U is a luminescent metal ion complex comprising a metal ion and a metal ion coordinating moiety covalently attached to the carrier molecule Z. In a related embodiment, the metal ion coordinating moiety of U is covalently attached to the carrier molecule Z through a linker. In another exemplary embodiment, the quencher of excited energy state is covalently attached to the carrier molecule Z through a linker.

In another aspect, the present invention provides a method for detecting a target analyte using luminescence. The method includes: (a) contacting the target analyte with a nucleic acid probe comprising a detector oligonucleotide; (b) binding the target analyte to the detector oligonucleotide portion of the nucleic acid probe to form a target analyte-detector oligonucleotide complex; (c) optionally separating the target analyte-detector oligonucleotide complex from the reaction solution; (d) exciting the target analyte-detector oligonucleotide complex with light; and (e) detecting an emitted photon from the target analyte-detector oligonucleotide complex.

In another aspect, the present invention provides a method for detecting a target analyte using fluorescence polarization. The method includes: (a) contacting the target analyte with a nucleic acid probe comprising a detector oligonucleotide; (b) binding the target analyte to the detector oligonucleotide portion of the nucleic acid probe to form a target analyte-detector oligonucleotide complex; (c) exciting the target analyte-detector oligonucleotide complex with plane polarized light; and (d) detecting the polarization of an emitted photon from the target analyte-detector oligonucleotide complex.

In another aspect, the present invention provides a method for evaluating the sequence in an oligonucleotide target sequence. The method includes: (a) contacting the target sequence with a nucleic acid probe comprising a detector oligonucleotide; (b) binding the target sequence to the detector oligonucleotide portion of the nucleic acid probe to form a target sequence-detector oligonucleotide complex; (c) applying a voltage to the target sequence-detector oligonucleotide complex; and (d) detecting the voltage flowing through the target sequence-detector oligonucleotide complex.

In another aspect, the present invention provides a method for detecting a target analyte using electrochemiluminescence. The method includes: (a) contacting the target analyte with a nucleic acid probe comprising a detector oligonucleotide; (b) binding the target analyte to the detector oligonucleotide portion of the nucleic acid probe to form a target analyte-detector oligonucleotide complex; (c) adding a coreactant to the target analyte-detector oligonucleotide complex; (d) applying a voltage to the target analyte-detector oligonucleotide complex to oxidize the coreactant and target analyte-detector oligonucleotide complex; (e) detecting the emitted light; and (f) returning the target analyte-detector oligonucleotide complex to its original oxidation state for another oxidation-emission cycle.

In another aspect, the present invention provides a method for detecting a nucleic acid target sequence using electrochemical detection. The method includes: a) contacting the target sequence with a nucleic acid probe comprising a detector oligonucleotide; (b) binding the target sequence to the detector oligonucleotide portion of the nucleic acid probe to form a target sequence-detector oligonucleotide complex; (c) applying an electrical potential to the target sequence-detector oligonucleotide complex to oxidize the detector oligonucleotide portion of the target sequence-detector oligonucleotide complex; and (g) returning the detector oligonucleotide portion of the target sequence-detector oligonucleotide complex to its original oxidation state.

In another aspect, the present invention provides a method for detecting the presence of a nucleic acid target sequence. The method includes: (a) contacting the target sequence with a nucleic acid probe comprising a detector oligonucleotide; (b) binding the target sequence to the detector oligonucleotide portion of the nucleic acid probe, thereby altering the conformation of the detector oligonucleotide, causing a change in a fluorescence parameter; and (c) detecting the change in the fluorescence parameter, thereby detecting the target sequence.

In another aspect, the invention provides method for detecting the presence of a nucleic acid target sequence, including the steps of: (a) contacting the target sequence with a nucleic acid probe comprising a detector oligonucleotide, wherein the detector oligonucleotide comprises a single-stranded target binding sequence and an intramolecularly associated secondary structure 5' to the target binding sequence; (b) hybridizing the target sequence to the detector oligonucleotide portion of the nucleic acid probe, wherein at least a portion of the target sequence forms a single stranded tail which is available for hybridization to the target sequence; (c) in a primer extension reaction, synthesizing a complementary strand using the intramolecularly associated secondary structure as a template, thereby dissociating the intramolecularly associated secondary structure and producing a change in a fluorescence parameter; (d) detecting the change in the fluorescence parameter, thereby detecting the nucleic acid target sequence.

In another aspect, the invention provides a method for detecting amplification of a target sequence. The method includes the use of an amplification reaction including the following steps: (a) contacting the target sequence with a nucleic acid probe comprising a detector oligonucleotide, wherein the detector oligonucleotide includes a single-stranded target binding sequence and an intramolecularly associated secondary structure 5' to the target binding sequence and at least a portion of the target sequence forms a single stranded tail which is available for hybridization to the target sequence; (b) hybridizing the target sequence to said detector oligonucleotide; (c) extending the hybridized detector oligonucleotide on the target sequence with a polymerase to produce a detector oligonucleotide extension product and separating the detector oligonucleotide extension product from the target sequence; (d) hybridizing a primer to the detector oligonucleotide extension product and extending the primer with the polymerase, thereby linearizing the intramolecularly associated secondary structure and producing a change in a fluorescence parameter; and (d) detecting the change in the fluorescence parameter, thereby detecting the target sequence.

In another aspect, the present invention provides a method for determining the presence of a target protein, wherein the target protein is an enzyme or a binding protein. The method comprises: (a) contacting the target protein with a peptide probe comprising luminescent metal ion complex; (b) exciting the luminescent complex; and (c) determining a fluorescence property of the sample, wherein the presence of the target protein in the sample results in a change in the fluorescence property of the luminescent complex.

In another aspect, the present invention provides a method for determining the presence of a target analyte, wherein the method comprises: (a) contacting the target analyte with a peptide probe comprising luminescent metal ion complex; (b) forming a peptide probe-target analyte complex; (c) optionally separating the peptide probe-target analyte complex from the reaction solution; (d) exciting the luminescent complex; and (e) detecting the emitted photons.

In a further aspect, the present invention provides a method for determining the presence of a target analyte, wherein the method comprises: (a) contacting the target analyte with a peptide probe; (b) forming a peptide probe-target analyte complex; (c) optionally separating the peptide probe-target analyte complex from the reaction solution; (d) adding a co-reactant to the peptide-target analyte complex; (d) applying a voltage to the peptide probe-target analyte complex to oxidize the co-reactant and peptide probe-target analyte complex; (e) detecting the emitted light from the oxidation reaction; and (g) returning the peptide probe-target analyte complex to its original oxidation state for another oxidation-emission cycle.

In another aspect, the invention provides another method for detecting amplification of a target sequence. The method includes the use of an amplification reaction including the following steps: (a) hybridizing the target sequence and the detector oligonucleotide of a dual labeled nucleic acid probe; (b) digesting the dual labeled nucleic acid probe with nucleic acid polymerase and producing a change in a fluorescence parameter; and (c) detecting the change in the fluorescence parameter, thereby detecting the target sequence.

In another aspect of the invention, the present invention provides a method for determining the presence of a target analyte, wherein the method comprises: (a) contacting the target analyte with a dual labeled peptide probe; (b) forming a dual labeled peptide probe-target analyte complex; (c) degrading the dual labeled peptide with a protease and producing a change in a fluorescence parameter; and (c) detecting the change in the fluorescence parameter, thereby detecting the presence of the target analyte.

DETAILED DESCRIPTION OF THE INVENTION

Introduction

Figure 1:
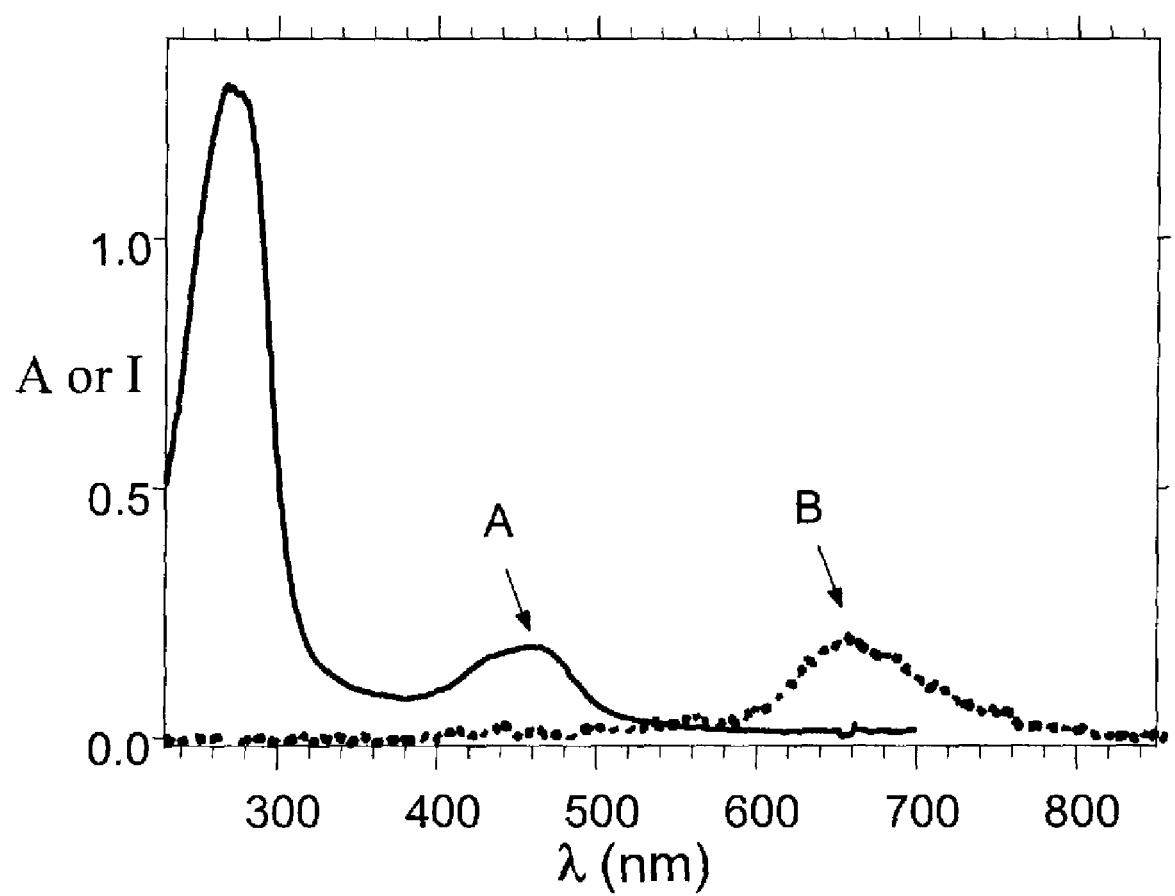
FIG. 1 illustrates absorption and emission spectra of 5'-T$_9$-mdT(Ru(bpy)$_2$(mcbpy)) with $\lambda_{ABSMAX}$=460 nm (arrow A) and $\lambda_{EMMAX}$=650 nm (Arrow B).

The present invention provides a family of luminescent metal ion complexes and components thereof that are useful for many purposes including, but not limited to, detection and isolation of target analytes, such as biomolecules. The present invention also provides methods for making both solid phase and solution phase luminescent metal ion complexes. In addition, the present invention provides methods of using the luminescent metal ion complexes as probes in assaying, detecting and isolating target analytes. Finally, the present invention provides methods for making and using dual labeled probes, wherein the dual labeled probes comprise a luminescent metal ion complex and a secondary probe.

Abbreviations

"MET," as used herein, refers to "Molecular Energy Transfer." MET is a generic term that encompasses the transfer of energy from one molecule or portion of a molecule to another. Examples of MET include, but are not limited to, transfer of nuclear magnetic resonance energy, electron transfer and transfer of excited state energy (e.g., Fluorescence Energy Transfer).

"FET," as used herein, refers to "Fluorescence Energy Transfer." "FRET," as used herein, refers to "Fluorescence Resonance Energy Transfer." These terms are used herein to refer to both radioactive and non-radiative energy transfer processes. For example, processes in which energy is emitted and those involving long range electron transfer are included within these terms. Throughout this specification, both of these phenomena are subsumed under the general term "donor-quencher energy transfer." In addition, FRET, as used herein, also includes luminescence resonance energy transfer (LRET) and is synonymous with Förster Resonance Energy Transfer.

Definitions

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

It is within the scope of the present invention to include one or more sites that are cleaved by the action of a "cleavage agent" other than an enzyme. Cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989).

The symbol ⌇, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" is meant to include oxygen (O), nitrogen (N), sulfur (S) and silicon (Si).

As used herein, "nucleic acid" means either DNA, RNA, single-stranded, double-stranded, or more highly aggregated hybridization motifs, and any chemical modifications thereof. Modifications include, but are not limited to, those which provide other chemical groups that incorporate additional charge, polarizability, hydrogen bonding, electrostatic interaction, and functionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

A "nucleobase" is a nucleoside or nucleotide. A "nucleoside" is a deoxyribose or ribose sugar, or derivative thereof, containing a nitrogenous base linked to the C1' of the sugar residue. A "nucleotide" is the C5' phosphate ester derivative of a nucleoside. The terms "nucleoside and "nucleotide" include those compounds having non-natural substituents at the C1', C2', C3', C5', and/or nitrogenous base (e.g., C2' alkyl, alkoxy, and halogen substituents).

"Polypeptide" refers to a polymer in which the monomers are amino acids and are joined together through amide bonds, alternatively referred to as a peptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

As used herein, "amino acid" refers to a group of water-soluble compounds that possess both a carboxyl and an amino group attached to the same carbon atom. Amino acids can be represented by the general formula NH$_2$—CHR—COOH where R may be hydrogen or an organic group, which may be nonpolar, basic acidic, or polar. As used herein, "amino acid" refers to both the amino acid radical and the non-radical free amino acid.

The term "hydroxy" is used herein to refer to the group —OH.

The term "amino" is used to describe primary amines, —NRR', wherein R and R' are independently H, alkyl, aryl or substituted analogues thereof. "Amino" encompasses "alkylamino" denoting secondary and tertiary amines and "acylamino" describing the group RC(O)NR'.

The term "alkoxy" is used herein to refer to the —OR group, where R is alkyl, aryl, or substituted analogues thereof. Suitable alkoxy radicals include, for example, methoxy, ethoxy, phenoxy, substituted phenoxy, benzyloxy, phenethyloxy, t-butoxy, etc.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e. RC(O)OR' or R'OC(O)R).

The term "heterocyclic" is used herein to describe a monovalent saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. CF$_3$), hydroxy, amino, alkoxy, alkylamino, acylamino, acyloxy, mercapto, etc.

"Biochip" refers to a solid substrate having a generally planar surface to which a probe is attached. Frequently, the surface of the biochip comprises a plurality of discrete locations having a bound probe.

A "target analyte," as used herein, means any microorganism, compound or molecule of interest for which a diagnostic test is desired. A target analyte can be, for example, a protein, peptide, carbohydrate, liposome, fatty acid, phospholipid, triacyl glycerol, polysaccharide, glycoprotein, hormone, receptor, antigen, antibody, pathogenic microorganism or virus, substrate, pharmaceutical, metabolite, narcotic, poison, transition state analog, cofactor, inhibitor, dye, nutrient, growth factor, antibodies, enzymes, and derivatives and combinations thereof, without limitation. The term can refer to a single component or a plurality of components in a given sample.

The term "oligonucleotide" defines a subset of "nucleic acid" comprising at least two nucleic acid monomer units.

The term "luminescent metal ion complex" as used herein refers to a chelated-metal ion complex capable of emitting energy.

The term "quencher of excited state energy" as used herein refers to a molecule capable of quenching excited state energy such as, but not limited to, electron transfer and energy transfer (e.g. dipole-dipole and collisional quenching).

The term "metal ion coordinating component" as used in herein refers to molecule capable of all modes of interaction with a metal ion, e.g. chelation.

A "ring," as used herein, refers to a substituted or unsubstituted cycloalkyl, substituted or unsubstituted heterocycloalkyl, substituted or unsubstituted aryl, and/or substituted or unsubstituted heteroaryl.

Metal Ion Coordinating Components of the Luminescent Metal Ion Complexes

In a first aspect, the present invention provides a family of metal ion coordinating components of a luminescent metal ion complex. The metal ion coordinating components of the present invention include at least one metal ion coordinating moiety.

Various metal ion coordinating moieties are useful in the current invention. One of skill will recognize that the applicable metal ion coordinating moiety will depend upon the metal ion being coordinated. Exemplary metal ion coordinating moieties of the present invention include ambidentate metal ion coordinating moieties (such as nitro or nitrite moieties), monodentate metal ion coordinating moieties (such as simple anions, $NH_3$, and $PMe_3$), bidentate metal ion coordinating moieties (such as 2,2'-bipyridine (bpy), mcbpy (4'-methyl-2,2'-bipyridine-4-carboxylic acid), ethylenediamine (en), diphenylphosphinoethane (dppe), acetylacetonate (acac), and oxalate (ox)), and polydentate metal ion coordinating moieties (such as substituted or unsubstituted crown ethers and ethylenediaminetetraacetic acid).

Typically, at least one metal ion coordinating moiety is covalently attached to a carrier molecule to form a metal ion coordinating component. Exemplary metal ion coordinating moieties include a reactive functional group that provides a locus for conjugation of the metal ion coordinating moiety to a carrier molecule.

The carrier molecule may be covalently bonded to more than one metal ion coordinating component to from multiple luminescent metal ion complexes. In an exemplary embodiment, the carrier molecule includes 2 to 30 metal ion coordination moieties. In a related embodiment, the carrier molecule includes 2 to 10 metal ion coordination moieties. In another related embodiment, the carrier molecule includes 2 to 5 metal ion coordination moieties.

Carrier molecules include a wide variety natural or synthetic polymers, rings, fused rings, and natural or synthetic biomolecules and biomolecule derivatives. Useful bimolecular carrier molecules include, for example, polypeptides, nucleic acids, sugars and oligosaccharides, liposomes, fatty acids, phospholipids, triacyl glycerols, steroids, and derivatives and combinations thereof.

The metal ion coordinating moiety can be covalently attached to any appropriate portion of the carrier molecule. Exemplary classes of reactions are those proceeding under relatively mild conditions. These include, but are not limited to nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example: (a) carboxyl groups and derivatives thereof including, but not limited to activated esters, e.g., N-hydroxysuccinimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides; (b) hydroxyl groups, which can be converted to esters, sulfonates, phosphoramidites, ethers, aldehydes, etc.; (c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups, which are capable of participating in Diels-Alder reactions such as, for example, maleimido groups; (e) aldehyde or ketone groups, allowing derivatization via formation of carbonyl derivatives, e.g., imines, hydrazones, semicarbazones or oximes, or via such mechanisms as Grignard addition or alkyllithium addition; (f) sulfonyl halide groups for reaction with amines, for example, to form sulfonamides; (g) thiol groups, which can be converted to disulfides or reacted with acyl halides, for example; (h) amine or sulfhydryl groups, which can be, for example, acylated, alkylated or oxidized; (i) alkenes, which can undergo, for example, cycloadditions, acylation, Michael addition, etc; (j) epoxides, which can react with, for example, amines and hydroxyl compounds; and (k) phosphoramidites and other standard functional groups useful in nucleic acid synthesis.

In an exemplary embodiment, the carrier molecule includes a reactive amine and the metal ion coordinating moiety includes a reactive carboxyl group. The carrier molecule it then covalently bonded to the metal ion coordinating moiety using any appropriate amide bond forming agent, such as those used in the art of peptide synthesis.

The reactive functional groups can be chosen such that they do not participate in, or interfere with, the reactions necessary to assemble or utilize the metal ion coordinating component. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In an exemplary embodiment, the carrier molecule is a polypeptide. A variety of methods of covalently attaching a metal ion coordinating component to a polypeptide are useful in the current invention. For example, polypeptides typically contain reactive functionalities at the amino acid side chains, the C-terminus, and/or the N-terminus. The inherent reactivity of these groups may be exploited to covalently attach a metal ion coordinating moiety to the polypeptide. For example, the carboxylate of an aspartate or glutamate side chain may be reacted with a carbodiimide to from an active ester intermediate, or with a carbodiimidazole to from an activated carbonyl intermediate. The active intermediates may then be coupled to a metal ion coordinating component comprising a free hydroxyl, thiol, amine, or hydrazine to from an ester, thioester amide, or hydrazide covalent linkage, respectively. A more detailed discussion of specific methods of covalently linking a metal ion coordinating moiety to a polypeptide is disclosed in Hermanson, BIOCONJUGATE TECHNIQUES, Academic Press, San Diego, 1996.

The metal ion coordinating moiety may be covalently attached to a full length polypeptide in solution either enzymatically or chemically. Alternatively, the metal ion coordinating component may be covalently attached to an amino acid and subsequently attached to a solid phase polypeptide either enzymatically or chemically, during or after polypeptide synthesis.

In another exemplary embodiment, the carrier molecule is a nucleic acid. A variety of methods of covalently attaching a metal ion coordinating component to a polypeptide are known in the art. For example, nucleic acids typically contain reactive functionalities at the internucleotide linkages, the 5'-carbon, the 3'-carbon, the 2'-carbon, the 1'-carbon, and/or the nitrogenous base.

In view of the well-developed body of literature concerning the conjugation of small molecules to nucleic acids, many other methods of attaching metal ion coordinating components to nucleic acids will be apparent to those of skill in the art. For example, rhodamine and fluorescein dyes are conveniently attached to the 5'-hydroxyl of an nucleic acid at the conclusion of solid phase synthesis by way of dyes derivatized with a phosphoramidite moiety (see, for example, Woo et al., U.S. Pat. No. 5,231,191; and Hobbs, Jr., U.S. Pat. No. 4,997,928).

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidite linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Oligonucleotides of the current invention, including detector oligonucleotides discussed below, can include at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

Oligonucleotides may also include one or more modified sugar moiety selected from the group including, but not limited to, arabinose, 2-fluoroarabinose, xylulose, and hexose.

In some embodiments, the oligonucleotide may include at least one modified phosphate backbone selected from the group including, but not limited to, a phosphorothioate, a phosphorodithioate, a phosphoramidothioate, a phosphoramidite, a phosphordiamidate, a boranophosphate, a methylphosphonate, an alkyl phosphotriester, and a formacetal or analog thereof.

Oligonucleotides of the invention can be synthesized by standard methods known in the art, e.g. by use of an automated DNA synthesizer (such as are commercially available from P.E. Biosystems, etc.) using commercially available amidite chemistries. Oligonucleotides bearing modified phosphodiester linking groups can be synthesized by methods known in the art. For example, phosphorothioate oligonucleotides may be synthesized by the method of Stein et al. (*Nuc. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked oligonucleotides will be apparent to those of skill in the art.

Once the desired oligonucleotide is synthesized, it may be cleaved from the solid support on which it was synthesized and treated, by methods known in the art, to remove any protecting groups present (e.g., ammonia treatment at 60° C.). In those embodiments in which a base-sensitive group is attached to the oligonucleotides (e.g., TAMRA), the deprotection will preferably use milder conditions (e.g., butylamine: water 1:3, 8 hours, 70° C.). Deprotection under these conditions is facilitated by the use of quick deprotect amidites (e.g., dC-acetyl, dG-dmf).

Following cleavage from the support and deprotection, the oligonucleotide is typically purified by any method known in the art, including chromatography, extraction and gel purification. In an exemplary embodiment, the oligonucleotide is purified using HPLC. The concentration and purity of the isolated oligonucleotide is preferably determined by measuring the optical density at 260 nm in a spectrophotometer.

The carrier molecule may be immobilized on a solid support or free in solution. Suitable solid supports for immobilization of a carrier molecule include polymolecular assemblies such as synthetic polymeric resins, gels, and biochips (including thin film coated biochips). Exemplary synthetic polymeric resins and gels include those composed, at least in part, of polystyrene and polyacrylic acids, amides, and esters; glass; polyols such as polyvinyl alcohol and polysaccharides such as agarose, cellulose, dextrans, ficols, heparin, glycogen, amylopectin, mannan, inulin, and starch.

The carrier molecule may be covalently bonded through a linker to any applicable label, such as a metal ion coordinating moiety, a quencher of excited energy state, and/or a luminescent metal ion complex. Linkers useful in the present invention are typically chosen to provide sufficient space between the carrier molecule and the label to allow the metal ion coordinating moiety to coordinate the desired metal ion. Linkers are typically substantially chemically inert so as to avoid undesired intramolecular or intermolecular cross reactions. Linkers can be hydrophilic (e.g., tetraethylene glycol, hexaethylene glycol, polyethylene glycol) or they can be hydrophobic (e.g., hexane, decane, etc.). In an exemplary embodiment, the linker is selected from $C_6$-$C_{30}$ alkyl groups, $C_6$-$C_{30}$ substituted alkyl groups, polyols, polyethers (e.g., poly(ethyleneglycol)), polyamines, polyamino acids, polysaccharides and combinations thereof.

In an exemplary embodiment, the linker is selected from substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In another related embodiment, the linker is selected from $C_1$-$C_{10}$ substituted or unsubstituted alkylene, 2 to 10 membered substituted or unsubstituted heteroalkylene, $C_3$-$C_8$ substituted or unsubstituted cycloalkylene, and 3 to 8 membered substituted or unsubstituted heterocycloalkylene. In another related embodiment, the linker comprises an unsubstituted polyethylene glycol.

In another exemplary embodiment, the linker has the formula:

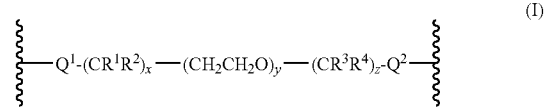

(I)

In Formula (I), x and z represent integers from 0 to 100 and y represents an integer from 1 to 100. $R^1$, $R^2$, $R^3$, and $R^4$ are individually selected from hydrogen, halogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and $OR^5$. $R^5$ is hydrogen or substituted or unsubstituted alkyl. $Q^1$ and $Q^2$ are individually selected from a bond, substituted or unsubstituted alkyl, and substituted or unsubstituted heteroalkyl.

In a related embodiment, $R^1$, $R^2$, $R^3$, and $R^4$ are individually selected from hydrogen, substituted or unsubstituted $C_1$-$C_5$ alkyl, and $OR^5$. $R^5$ is hydrogen or substituted or unsubstituted $C_1$-$C_5$ alkyl. In a further related embodiment, $R^1$, $R^2$, $R^3$ and $R^4$ are hydrogen.

In another related embodiment, x and z represent integers from 0 to 10 and y represents and integer from 1 to 10. In a further related embodiment, x and z represent integers from 0 to 5 and y represents and integer from 1 to 5.

In yet another related embodiment, $Q^1$ and $Q^2$ are individually selected from a bond, —NH—, —C(O)—, —C(O) NH—, —C(O)O—, —O—, —S—, —S—S—, and —N═N—. In a further related embodiment, $Q^1$ is —NH— and $Q^2$ is, —C(O)NH—. In yet a further related embodiment, x is 0, y is 3, z is 1, and $R^3$ and $R^4$ are hydrogen.

The metal ion coordinating moieties may include a substituted or unsubstituted heterocycloalkyl or substituted or unsubstituted heteroaryl. Typically, the heteroatom in the heterocycloalkyl or heteroaryl is capable of coordinating a metal ion. Preferably, the heteroatom capable of coordinating the metal ion is nitrogen or oxygen.

In an exemplary embodiment, the metal ion coordinating moiety includes at least one ring structure selected from the group of substituted or unsubstituted heterocycloalkyl and substituted or unsubstituted heteroaryl. In another exemplary embodiment, the metal ion coordinating moiety comprises two or three ring structures selected from the group of substituted or unsubstituted heterocycloalkyl or substituted or unsubstituted heteroaryl. In another exemplary embodiment, the metal ion coordinating moiety comprises from one to eight ring structures selected from the group of substituted or unsubstituted heterocycloalkyl or substituted or unsubstituted heteroaryl.

The metal ion coordinating moieties may include two metal ion coordination sites, also referred to herein as a bidentate metal ion coordinating moiety. Bidentate metal ion coordinating moieties are well known in the art (Bashkin et al., *J. Org. Chem.*, 61: 2314-2321 (1996)); Ciana et al., *J. Org. Chem.*, 54: 1731-1735 (1996); Hu et al., *Inorg. Chem.*, 39 2500-2504 (2000)). A broad range of bidentate metal ion coordinating moieties are useful in the current invention. In an exemplary embodiment, the bidentate metal ion coordinating moiety is selected from substituted or unsubstituted bipyridyl, substituted or unsubstituted phenanthroline, substituted or unsubstituted 2,4 pentanediene, substituted or unsubstituted hydroxamate, substituted or unsubstituted terpyridine, substituted or unsubstituted dipyridophenazine, and substituted or unsubstituted acetylacetonate. In another exemplary embodiment, the bidentate metal ion coordinating moiety has the formula:

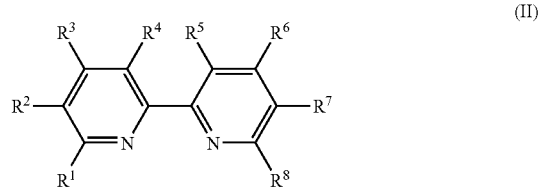

(II)

In Formula (II), $R^1$, $R^2$, $R^3$, $R^4$, $R^5$, $R^6$, $R^7$, and $R^8$ are members independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^A$, $NR^BR^C$, $NR^DOR^E$, $SR^F$, and $SO_2R^G$. $R^A$, $R^B$, $R^C$, $R^D$, $R^E$, $R^F$, and $R^G$ are independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^4$ and $R^5$ together with the atom to which they are attached are optionally joined to form a 3 to 8 membered ring. In some embodiments, at least one of $R^1$, $R^2$, $R^3$, $R^4$, $R^5$, $R^6$, $R^7$, and $R^8$ is attached to a linker to conjugate the moiety to a carrier molecule. One of skill will immediately recognize that where $R^1$, $R^2$, $R^3$, $R^4$, $R^5$, $R^6$, $R^7$, and $R^8$ is attached to a linker, the attached substituent forms a divalent radical. For example, where $R^3$ is a substituted or unsubstituted alkyl, the substituted or unsubstituted alkyl becomes the corresponding divalent radical substituted or unsubstituted alkylene when $R^8$ is attached to a linker. Thus, where $R^1$, $R^2$, $R^3$, $R^4$, $R^5$, $R^6$, $R^7$, and $R^8$ is attached to a linker, $R^1$, $R^2$, $R^3$, $R^4$, $R^5$, $R^6$, $R^7$, and $R^8$ is selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, and substituted or unsubstituted heteroarylene. In an exemplary embodiment, only one of $R^1$, $R^2$, $R^3$, $R^4$, $R^5$, $R^6$, $R^7$, and $R^8$ is attached to the linker.

In a related embodiment, $R^1$, $R^2$, $R^3$, $R^4$, $R^5$, $R^6$, $R^7$, and $R^8$ are members independently selected from hydrogen, substituted or unsubstituted alkyl, substituted and unsubstituted heterocycloalkyl, substituted or unsubstituted aryl, and substituted or unsubstituted heteroaryl. In a further related embodiment, $R^1$, $R^2$, $R^3$, $R^4$, $R^5$, $R^6$, $R^7$, and $R^8$ are members independently selected from hydrogen, substituted or unsubstituted $C_1$-$C_{10}$ alkyl, substituted or unsubstituted 5 to 7 membered heterocycloalkyl, substituted or unsubstituted aryl, and substituted or unsubstituted heteroaryl. In yet a further related embodiment, $R^1$, $R^2$, $R^3$, $R^4$, $R^5$, $R^6$, $R^7$, and $R^8$ are members independently selected from hydrogen, substituted or unsubstituted $C_1$-$C_5$ alkyl, substituted or unsubstituted 5 to 7 membered heterocycloalkyl, substituted or unsubstituted aryl, and substituted or unsubstituted heteroaryl.

In another related embodiment, $R^4$ and $R^5$ are members independently selected from hydrogen, substituted or unsubstituted alkyl, substituted or unsubstituted heteroaryl, substituted or unsubstituted aryl, substituted or unsubstituted heterocycloalkyl, or together with the atom to which they are joined are optionally joined to form a 5 to 7 membered ring. in a further related embodiment, $R^4$ and $R^5$ are members independently selected from hydrogen, $C_1$-$C_{10}$ alkyl, substituted or unsubstituted heteroaryl, substituted or unsubstituted aryl, substituted or unsubstituted 5 to 7 membered heterocycloalkyl, or together with the atom to which they are joined are optionally joined to form a 5 to 7 membered ring.

In another related embodiment, $R^1$, $R^2$, $R^3$, $R^5$, $R^6$, $R^7$, are hydrogen, $R^3$ is a bond attached to a linker, and $R^6$ is $C_1$-$C_{10}$ unsubstituted alkyl. In another related embodiment, $R^6$ is $C_1$-$C_5$ unsubstituted alkyl. In a further related embodiment, $R^6$ is methyl.

In another related embodiment, $R^A$, $R^B$, $R^C$, $R^D$, $R^E$, $R^F$, $R^F$, and $R^G$ are independently selected from the group consisting of hydrogen, substituted or unsubstituted $C_1$-$C_5$ alkyl, substituted or unsubstituted 2 to 5 membered heteroalkyl, substituted or unsubstituted $C_3$-$C_7$ cycloalkyl, substituted or unsubstituted 3 to 7 membered heterocycloalkyl, substituted or unsubstituted aryl, and substituted or unsubstituted heteroaryl.

Other useful metal ion coordinating components include, but are not limited to, bipyridyl, phenanthroline, dpop, dpb, dpq, 2,2-dpp, 2,5-dpp, Me$_4$phen, dppene, Me$_2$PPh, das, ttpy, Me$_2$SO, dppm, py, dppb, dpae.

Nucleic Acid Metal Ion Coordinating Components

In another aspect, the current invention provides nucleic acid metal ion coordinating component of a luminescent metal ion complex having: (i) a nucleobase comprising a nitrogenous base; (ii) a linker covalently bonded to the nitrogenous base; and (iii) a metal ion coordinating moiety covalently bonded to the linker to form the nucleic acid metal ion coordinating component of the luminescent metal ion complex. Linkers and metal ion coordinating components discussed above are equally useful for nucleic acid metal ion coordinating components.

In an exemplary embodiment, the metal ion coordinating moiety is covalently attached to the nitrogenous base of the 3'-nucleobase of the nucleic acid metal ion coordinating component. Covalently attaching the metal ion coordinating moiety to the 3'-nucleotide provides advantages where the nucleic acid metal ion component is produced synthetically via solid phase oligonucleotide synthesis. By avoiding the use of expensive phosphoramidites containing metal ion coordinating moieties, the cost of producing nucleic acid metal ion coordinating components is dramatically decreased. In addition, higher synthetic yields are achieved for singly and multi-labeled probes.

The nucleic acid metal ion coordinating components of the present invention may contain more than one metal ion coordinating moiety. In an exemplary embodiment, the nucleic acid metal ion coordinating component includes two metal ion coordination moieties. In another exemplary embodiment, the nucleic acid metal ion coordinating component comprises from 2 to 30 metal ion coordination moieties. In a related embodiment, the nucleic acid metal ion coordinating component contains 2 to 10 metal ion coordination moieties. In another related embodiment, the nucleic acid metal ion coordinating component contains 2 to 5 metal ion coordination moieties.

Where the nucleic acid metal ion coordinating components of the present invention may contain more than one metal ion coordinating moiety, the metal ion coordinating moieties may be attached to adjacent nucleobases. Alternatively, there may be one or more nucleobases between the metal ion coordinating moieties. In an exemplary embodiment, 1 to 30 nucleobases separate the metal ion coordinating moieties. In another exemplary embodiment, 1 to 10 nucleobases separate the metal ion coordinating moieties. In another exemplary embodiment, 1 to 5 nucleobases separate the metal ion coordinating moieties. In another exemplary embodiment, 1 nucleobase separates the metal ion coordinating moieties. In another exemplary embodiment, the metal ion coordinating moieties are attached to every other nucleobase. In another exemplary embodiment, the metal ion coordinating moieties are attached to every third nucleobase. Exemplary nucleic acid metal ion coordinating components containing more than one metal ion coordinating moiety are present in Examples 1, 3, and 4 below.

Any appropriate metal ion coordinating moiety and linker discussed above may be used with the nucleic acid metal ion coordinating components. In an exemplary embodiment, the metal ion coordinating moiety of the nucleic acid metal ion coordinating component is a bidentate metal ion coordinating component. Thus, in an exemplary embodiment, the nucleic acid metal ion coordinating component includes (i) a nucleobase comprising a nitrogenous base; (ii) a linker covalently bonded to the nitrogenous base; and (iii) a bidentate metal ion coordinating moiety covalently bonded to the linker of the nucleic acid metal ion coordinating component of the luminescent metal ion complex.

Nitrogenous bases are typically derivatives of purine or pyrimidine (i.e. substituted or unsubstituted purine or substituted or unsubstituted pyrimidine). One skilled in the art will recognize that a wide range of natural and non-natural nitrogenous bases are useful in the current invention, including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethyl guanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine. Nitrogenous bases may comprise a reactive group to which the linker is attached. Useful reactive functional groups are discussed in detail above. In an exemplary embodiment, the nitrogenous base is s substituted or unsubstituted pyridine or substituted or unsubstituted pyrimidine. In another exemplary embodiment, the nitrogenous base is selected from guanine, thymine, cytosine, adenine, and uracil.

In another exemplary embodiment, the nucleic acid metal ion coordinating component further comprises a non-nucleic acid spacer bonded to the nucleobase. A solid support is covalently bound to the non-nucleic acid spacer. In a further embodiment, the non-nucleic acid spacer is attached to the nucleobase through the 3'C of the nucleobase.

In another exemplary embodiment, the nucleobase of the metal ion coordinating component is covalently bonded to a oligonucleotide. In a related embodiment, the oligonucleotide is attached to the 5'C of the nucleobase through a phosphoester bond or derivative thereof.

In another exemplary embodiment, the nucleic acid metal ion coordinating component further comprises additional metal ion coordinating moieties. In a related embodiment, the additional metal ion coordinating moieties are covalently bonded to a carrier molecule. The carrier molecule is covalently attached to the nucleobase. In a related embodiment, the carrier molecule is an oligonucleotide. In a further related embodiment, the oligonucleotide is covalently attached to 1 to 10 additional metal ion coordinating moieties.

The nucleic acid metal ion coordinating component may be attached to a solid support or free in solution. Useful solid supports are discussed above, and include resins, gels, and biochips (including thin film coated biochips). Exemplary synthetic polymeric resins and gels include those composed, at least in part, of polystyrene and polyacrylic acids, amides, and esters; glass; polyols such as polyvinyl alcohol and polysaccharides such as agarose, cellulose, dextrans, ficols, heparin, glycogen, amylopectin, mannan, inulin, and starch. Typically, a spacer connects the nucleic acid metal ion coordinating components to the solid support.

In an exemplary embodiment, the nucleic acid metal ion coordinating component has the formula:

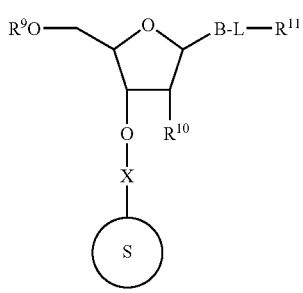

(III)

In Formula (III), $R^9$ is selected from hydrogen, substituted or unsubstituted alkyl, substituted or unsubstituted aryl, substituted or unsubstituted heteroaryl, substituted and unsubstituted heterocycloalkyl, a nucleobase or oligonucleotide. $R^{10}$ represents hydrogen, substituted or unsubstituted alkyl, substituted or unsubstituted aryl, substituted or unsubstituted heteroaryl, substituted and unsubstituted heterocycloalkyl, halogen, or $OR^{12}$. $R^{12}$ is selected from hydrogen, substituted or unsubstituted alkyl, and substituted or unsubstituted heteroalkyl. $R^{11}$ is a metal ion coordinating component, X is a non-nucleic acid spacer, B is a nitrogenous base, L is a linker, and S is a solid support.

Non-nucleic acid spacers include any spacer that does not contain a nucleobase. Non-nucleic acid spacers are well known in the art. See Eckstein, editor, Nucleic Acids and Analogues: A Practical Approach (IRL Press, Oxford, 1991). Any appropriate non-nucleic acid spacer may be used in the present invention. Typically, non-nucleic acid spacers are chosen to provide efficient coupling of the first nucleobase and removal of the nucleic acid metal ion coordinating component from the solid support while sufficiently maintaining the structural integrity of the nucleic acid metal ion coordinating component. In an exemplary embodiment, the nucleic acid spacer is selected from $C_6$-$C_{30}$ alkyl, $C_6$-$C_{30}$ substituted alkyl, polyols, polyethers (e.g., poly(ethyleneglycol)), polyamines, polyamino acids, polysaccharides and combinations thereof. Non-nucleic acid spacers are preferably provided with a group that can be cleaved to release nucleic acids, such as, for example, the nucleic acid metal ion coordinating components or a nucleic acid luminescent metal ion complex. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) non nucleic acid spacers are commercially available from suppliers such as Pierce.

In a related embodiment, $R^9$ is an oligonucleotide containing from 1 to 100 nucleobases. In another related embodiment, $R^9$ is an oligonucleotide containing from 1 to 50 nucleobases. As defined above, a nucleobase may contain non-natural substituents at the C1', C2', C3', C5', and/or nitrogenous base (e.g., C2' alkyl, alkoxy, and halogen substituents).

In another related embodiment, $R^{10}$ is hydrogen or —OH.

In another related embodiment B represents guanine, thymine, cytosine, adenine or uracil. In another exemplary embodiment, B is a thymine. In a related embodiment, the linker is covalently bonded to a thymine amine.

In another exemplary embodiment, the nucleic acid metal ion coordinating component has the formula:

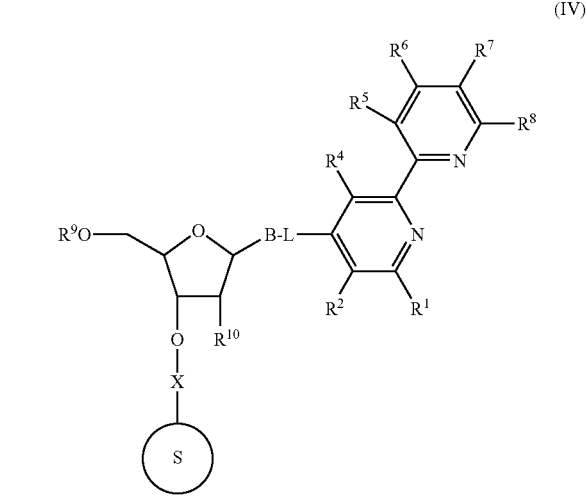

(IV)

In the Formula (IV), $R^1$, $R^2$, $R^4$, $R^5$, $R^6$, $R^7$, and $R^8$ are as defined in Formula (II); and $R^9$, $R^{10}$, B, L and X are as defined in Formula (III).

In a related embodiment, the nucleic acid metal ion coordinating component has the formula:

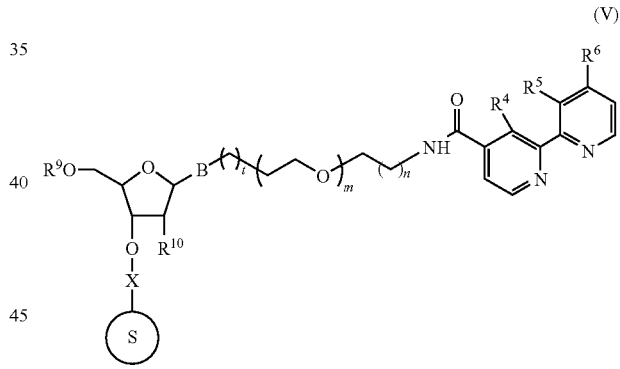

(V)

In Formula (V), $R^4$, $R^5$, and $R^6$ are as defined in Formula (II); and $R^9$, $R^{10}$, B and X are as defined in Formula (III). The symbols t and n represent integers from 0 to 10 and m represents and integer from 1 to 10. In a further related embodiment, t and n represent integers from 0 to 5 and m represents and integer from 1 to 5.

In another exemplary embodiment, the nucleic acid metal ion coordinating component has the formula:

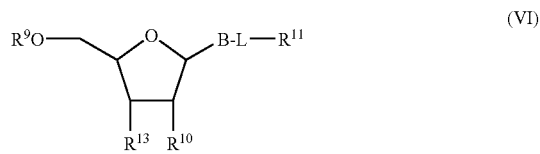

(VI)

In Formula (VI), $R^9$, $R^{10}$, $R^{11}$, B and L are as defined in Formula III. $R^{13}$ is selected from hydrogen, substituted or unsubstituted alkyl, substituted or unsubstituted aryl, substituted or unsubstituted heteroaryl, substituted and unsubstituted heterocycloalkyl, halogen, and $OR^{14}$. $R^{14}$ is selected from hydrogen, substituted or unsubstituted alkyl, phosphoramidite, and H-phosphonate. In a related embodiment, $R^{13}$ is hydrogen or —OH.

In another exemplary embodiment, the nucleic acid metal ion coordinating component has the formula:

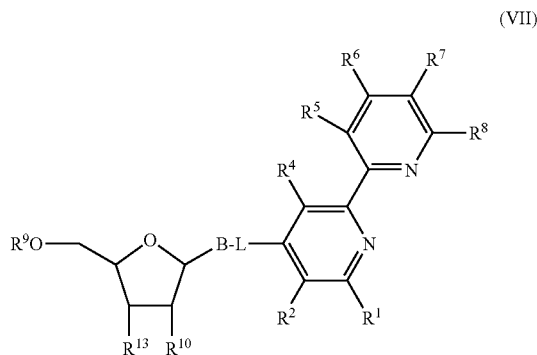

(VII)

In Formula (VII), $R^1$, $R^2$, $R^4$, $R^5$, $R^6$, $R^7$, and $R^8$ are as defined in Formula (II); $R^9$, $R^{10}$, B, and L are as defines in Formula (III); and $R^{13}$ is as defined in Formula (VI).

In another embodiment, the nucleic acid metal ion coordinating component has the formula:

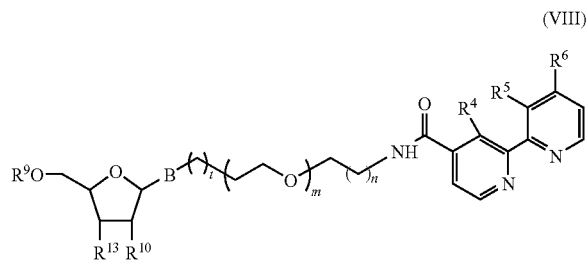

(VIII)

In Formula (VIII), $R^4$, $R^5$, $R^6$ are as defined in Formula (II); $R^9$, $R^{10}$, and B are as defined in Formula (III); t, m, and n are as defines in Formula (V); and $R^{13}$ is as defined in Formula (VI).

Luminescent Metal Ion Complexes

In another aspect, the present invention provides luminescent metal ion complexes that include a metal ion coordinated to one or more metal ion coordinating components of the present invention. The metal ion coordinating components of the present invention include at least one metal ion coordinating moiety, which are described in detail above.

The luminescent metal ion complexes of the present invention are typically capable of absorbing energy and thereafter emitting the excited state energy. Modes of emitting excited state energy are well known in the art and include, for example, photon emission, electron transfer and energy transfer (e.g. dipole-dipole and collisional quenching). Modes of absorbing or quenching light energy include light absorbance or quenching and electrical energy absorbance or quenching. Many mechanisms of excited state energy quenching are well known in the art, such as Dexter mechanism quenching and static quenching. The present invention is not limited by any particular quenching mechanism.

In an exemplary embodiment, the luminescent metal ion complexes are capable of emitting light and have relatively high fluorescence detectability. The factors that affect detectability of fluorescence in solution are well known and well documented in the literature (Haugland, *Molecular Probes Handbook of Fluorescent Probes and Research Chemicals*, (1992)) and include strong absorbance, high quantum yields in the solvent used for fluorescence detection and photolytic stability. Other properties that may affect the selection of a luminescent metal ion complexes include the emission and excitation wavelengths, chemical stability, ease of synthesis, and freedom from nonspecific quenching by ions or other agents that may be present in the sample.

The luminescent metal ion complexes may include a fluorescent dye, or derivative thereof, chosen from the group of xanthenes, such as fluoresceins, benzofluoresceins, naphthofluoresceins, eosins, erythrosins, rosamines, rhodamines (e.g., tetramethylrhodamine, sulforhodamines such as TEXAS RED dye), or rhodols. Additional useful fluorophores include benzimidazoles, phenoxazines (e.g., resorufin, nile blue), ethidiums, propidiums, anthracyclines, mithramycins, acridines, actinomycins, styryl dyes, carbocyanines, merocyanines, coumarins (e.g. 7-amino-4-methylcoumarins), pyrenes, chrysenes, stilbenes, carbazines, porphyrins, anthracenes, naphthalenes (e.g. dansyl, 5-dimethylamino-1-naphthalenesulfonyl), salicylic acids, anthranilic acids, benz-2-oxa-1,3-diazoles (also known as benzofurazans) (e.g. 4-amino-7-nitrobenz-2-oxa-1,3-diazole), fluorescamine, dipyrrometheneboron difluorides, and dibenzopyrrometheneboron difluorides.

The luminescent metal ion complexes of the present invention will have any appropriate number of metal ion coordinating components sufficient to chelate the desired metal. For example, where the metal ion is $Cu^{2+}$, the luminescent metal ion complex may include three bidentate metal ion coordinating moieties. Alternatively, the luminescent metal ion complex may include one bidentate metal ion coordinating component and four monodentate metal ion coordinating components. In another exemplary embodiment, the luminescent metal ion complexes include from one to six metal ion coordinating components. In another exemplary embodiment, the metal ion is chelated with 2, 3, 4, 5, or 6 metal ion coordinating components.

At least one of the metal ion coordinating moieties of the metal ion coordinating components is covalently bound to a carrier molecule. In some embodiments, the luminescent metal ion complexes may include 2 or more metal ion coordinating moieties covalently attached to a carrier molecule. For example, 3 bidentate metal ion coordinating moieties covalently attached to a nucleic acid, a polypeptide, and a fatty acid, respectively, may be combined to form a luminescent metal ion complex that chelates a ruthenium ion ($Ru^{2+}$).

To increase the detectable signal intensity, multiple luminescent metal ion complexes may be formed on a single carrier molecule. Where multiple luminescent metal ion complexes are formed on a single molecule, the complexes are typically selected to minimize self-quenching. Self-quenching occurs when the emitted energy from one complex is absorbed by another complex in the ground state. Self-quenching may be minimized using a variety of methods, including the use of luminescent metal ion complexes with a sufficiently large Stokes shift (absorption and emission curves overlap). Thus, in an exemplary embodiment, multiple luminescent metal ion complexes are formed on a single carrier molecule wherein the luminescent metal ion complexes have a sufficiently large Stokes shift to minimize self-quenching.

In an exemplary embodiment, the carrier molecule contains at least 500 luminescent metal ion complexes. In another exemplary embodiment, the carrier molecule contains at least 100 luminescent metal ion complexes. In another exemplary embodiment, the carrier molecule contains from 30-100 luminescent metal ion complexes. In another exemplary embodiment, the from 2 to 30 luminescent metal ion complexes. In a related embodiment, the carrier molecule contains from 2 to 10 luminescent metal ion complexes. In another related embodiment, the carrier molecule contains from 2 to 5 luminescent metal ion complexes.

Any appropriate metal ion is useful in the current invention. Metal ions are typically selected that are sufficiently chelated by the metal ion coordination components of the current invention. Exemplary metal ions include lanthanide metals and transition metals. In an exemplary embodiment, the metal ion is selected from iron, ruthenium, osmium, rhenium, copper, or a lanthanide metal. In a related embodiment, the metal ion ruthenium, osmium, or rhenium. In another related embodiment, the metal ion is ruthenium.

In another exemplary embodiment, the electrochemical and spectral properties of the luminescent metal ion complexes are tuned or adjusted by changing one or more of the metal ion coordinating moieties. For example, a substituted or unsubstituted bipyridyl metal ion coordinating moiety may by substititued with a substituted or unsubstituted phenanthroline, substituted or unsubstituted 2,4 pentanediene, substituted or unsubstituted hydroxamate, substituted or unsubstituted terpyridine, substituted or unsubstituted dipyridophenazine, or substituted or unsubstituted acetylacetonate.

In an exemplary embodiment, the invention provides a luminescent metal ion complex including a metal ion coordinated to a first metal ion coordinating component covalently bound to a carrier molecule. In a related embodiment, the carrier molecule is a nucleic acid or a polypeptide. In another related embodiment, the luminescent metal ion complex further includes at least one additional metal ion coordinating component. In a further related embodiment, the additional metal ion coordinating components are not covalently bound to a carrier molecule. In another related embodiment, the luminescent metal ion complex further includes 1 to 5 additional metal ion coordinating components.

In another exemplary embodiment, the invention provides a luminescent metal ion complex including a metal ion coordinated to a first metal ion coordinating component, a second metal ion coordinating component, and a third metal ion coordinating component. The first metal ion coordinating includes: (i) a nucleobase comprising a nitrogenous base; (ii) a linker covalently bonded to the nitrogenous base; and (iii) a first metal ion coordinating moiety covalently bonded to the linker to form the luminescent metal ion complex. In a related embodiment, the luminescent metal ion complex further include two additional metal ion coordinating components that are not covalently bound to a carrier molecule. In another related embodiment, the metal ion coordinating moiety is a bidentate metal ion coordinating moiety. In a further related embodiment, the bidentate metal ion coordinating moiety is a substituted or unsubstituted bipyridinyl.

In another exemplary embodiment, the luminescent metal ion complex has the formula:

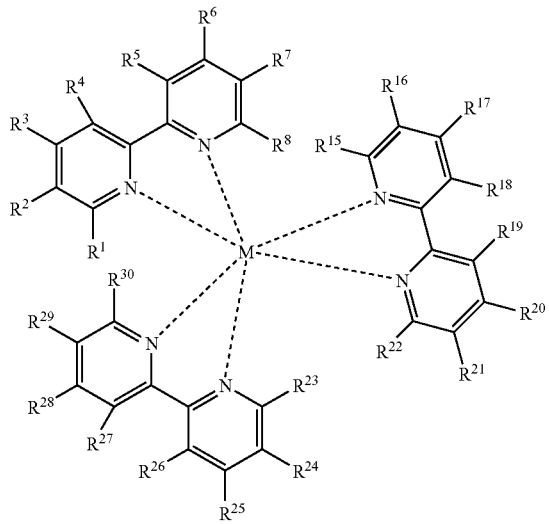

(IX)

In Formula (IX), $R^1$, $R^2$, $R^3$, $R^4$, $R^5$, $R^6$, $R^7$, and $R^8$ are as defined above in Formula (II). $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^A$, $NR^BR^C$, $NR^DOR^E$, $SR^F$, and $SO_2R^G$. $R^A$, $R^B$, $R^C$, $R^D$, $R^E$, $R^F$, and $R^G$ are as defined in Formula (II) above. $R^{18}$ and $R^{19}$ together with the atom to which they are attached are optionally joined to form a 3 to 8 membered ring. $R^{26}$ and $R^{27}$ are optionally joined together with the atoms to which they are attached to from a 3 to 8 membered ring. M is a metal ion selected from a lanthanide metal and a transition metal.

In a related embodiment, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are independently selected from hydrogen, substituted or unsubstituted alkyl, substituted and unsubstituted heterocycloalkyl, substituted or unsubstituted aryl, and substituted or unsubstituted heteroaryl. In a further related embodiment, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are member independently selected from hydrogen, substituted or unsubstituted $C_1$-$C_{10}$ alkyl, substituted or unsubstituted 5 to 7 membered heterocycloalkyl, substituted or unsubstituted aryl, and substituted or unsubstituted heteroaryl. In yet a further related embodiment, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are members independently selected from hydrogen, substituted or unsubstituted $C_1$-$C_5$ alkyl, substituted or unsubstituted 5 to 7 membered heterocycloalkyl, substituted or unsubstituted aryl, and substituted or unsubstituted heteroaryl. In another related embodiment, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are hydrogen.

In another related embodiment, M represents ruthenium, osmium, or rhenium.

In another exemplary embodiment, the luminescent metal ion complex is stable to nucleic acid deprotection and cleavage agents.

Nucleic Acid Luminescent Metal Ion Complexes

In another aspect, the present invention provides nucleic acid luminescent metal ion complexes having: (i) a nucleobase having a nitrogenous base; (ii) a linker covalently bonded to the nitrogenous base; (iii) a metal ion coordinating moiety covalently bonded to the linker; and (iv) a metal ion coordinated to the metal ion coordinating moiety.

In an exemplary embodiment, the nucleic acid luminescent metal ion complex has the formula:

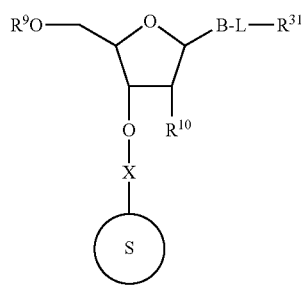
(X)

In Formula (X), $R^9$, $R^{10}$, X, B and L are as defined in Formula (III). $R^{31}$ is a luminescent metal ion complex as described above.

In another exemplary embodiment, the nucleic acid luminescent metal ion complex has the formula:

In Formula (XI), $R^1$, $R^2$, $R^4$, $R^5$, $R^6$, $R^7$, and $R^8$ are as defines in Formula (II); $R^9$, $R^{10}$, B, L and X are as defined in Formula (III); $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, and M are as defined in Formula (IX).

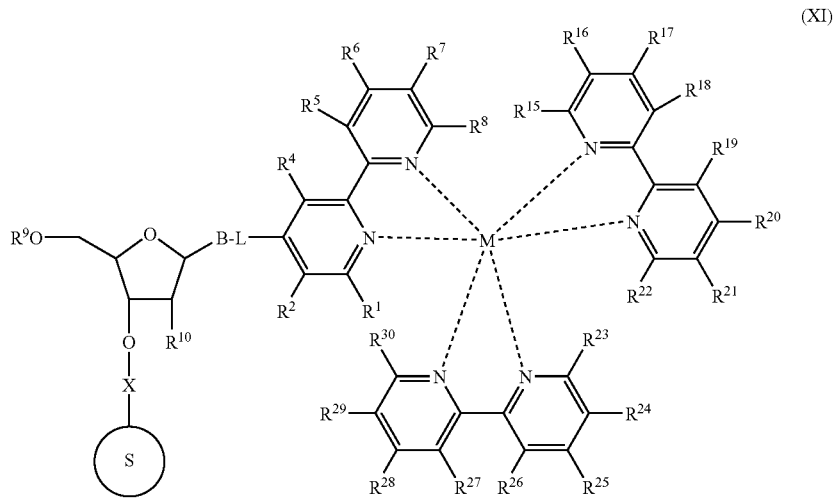
(XI)

In a related embodiment, the nucleic acid luminescent metal ion complex has the formula:

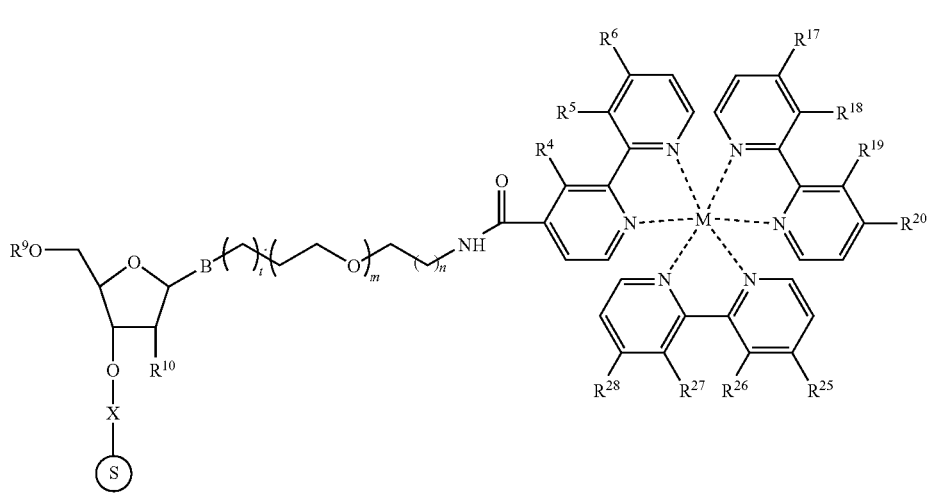
(XII)

In Formula (XII), $R^4$, $R^5$, and $R^6$ are as defines in Formula (II); $R^{17}$, $R^{18}$, $R^{19}$, $R^{20}$, $R^{25}$, $R^{26}$, $R^{27}$, $R^{28}$, and M are as defines in Formula (IX); $R^9$, $R^{10}$, B, L, and X are as defined in Formula (III); and t, m, and n are as defined in Formula (V).

In another exemplary embodiment, the nucleic acid luminescent metal ion complex has the formula:

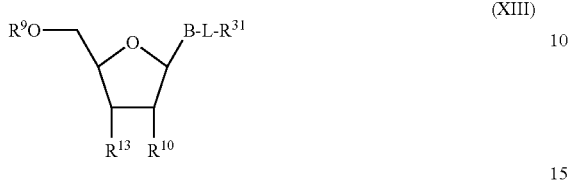

(XIII)

In Formula (XIII), $R^9$, $R^{10}$, B, and L are as defined in Formula (III); $R^{13}$ is as defined in Formula (VI); and $R^{31}$ is as defined in Formula (X).

In another exemplary embodiment, the nucleic acid luminescent metal ion complex has the formula:

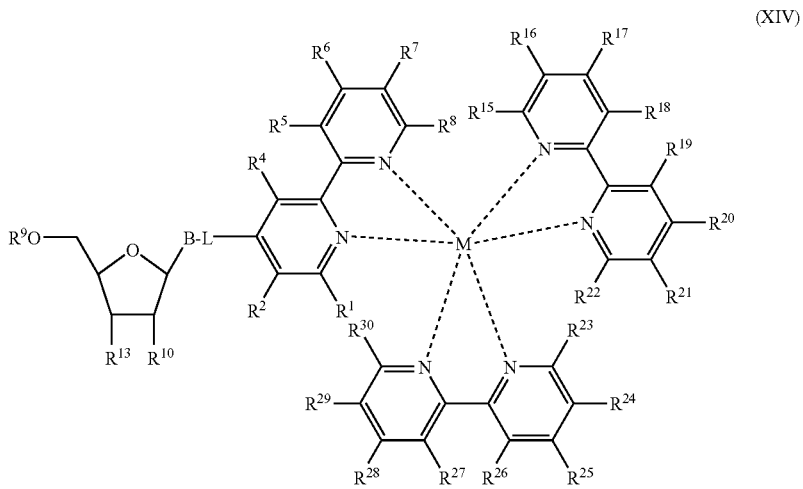

(XIV)

In Formula (XIV), $R^1$, $R^2$, $R^4$, $R^5$, $R^6$, $R^7$, and $R^8$ are as defines in Formula (II); $R^9$, $R^{10}$, B, and L are as defined in Formula (III); $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, and M are as defined in Formula (IX); and $R^{13}$ is as defined in Formula (VI).

In another embodiment, the nucleic acid luminescent metal ion complex has the formula:

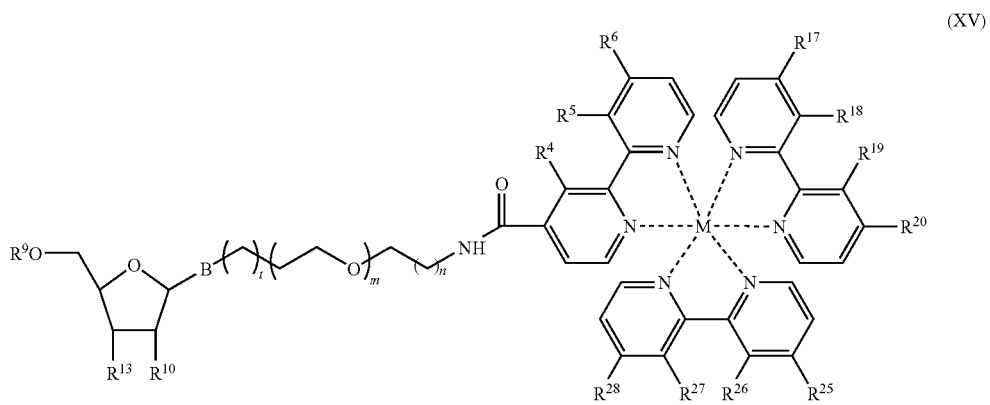

(XV)

In Formula (XV), $R^4$, $R^5$, and $R^6$ are as defines in Formula (II); $R^{17}$, $R^{18}$, $R^{19}$, $R^{20}$, $R^{25}$, $R^{26}$, $R^{27}$, $R^{28}$, and M are as defines in Formula (IX); $R^9$, $R^{10}$, B, and L are as defined in Formula (III); t, m, and n are as defined in Formula (V); and $R^{13}$ is as defined in Formula (VI). Further examples of a nucleic acid luminescent metal ion complexes with ruthenium metal ion ruthenium are presented in the Examples section below.

In another aspect, the invention provides luminescent metal ion complex between a metal ion and a first metal ion coordinating component, a second metal ion coordinating component and a third metal ion coordinating component. The first metal ion coordinating component of the luminescent metal ion complex comprises a nucleic acid attached to a solid support. The nucleic acid comprises a 5' amino group covalently bonded to a metal ion coordinating moiety. In an exemplary embodiment, the first metal ion coordinating moiety is methyl-carboxy bipyridyl, the second metal ion coordinating component is bipyridyl and the third metal ion coordinating component is bipyridyl. (see Examples section, Preparation of Ru(bpy)$_2$(mcbpy)).

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention.

Scheme 1

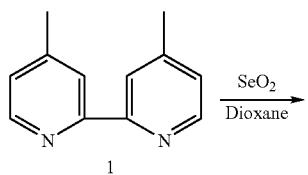

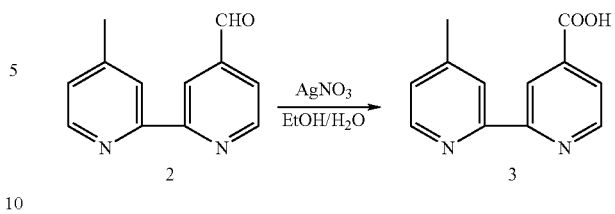

One method of synthesizing compounds of the invention is set forth in Schemes 1 and 2. In Scheme 1, 4'-methyl-2,2'-bipyridine-4-carboxylic acid 3 was synthesized following the procedures of Khan et al., Inorg. Chem., 38: 2411-2415 (1999). In an exemplary embodiment, the carboxy bipyridine 3 was then used to synthesize the compounds of the invention as outlined in Scheme 2.

To a solution of phosphorus oxychloride, triazole and triethylamine was added 5'-(4,4'dimethoxytrityl)-3'-O-tertbutyldimethysilyl thymidine 4 and 4,7-10 trioxo-1,13 tridecane diamine. The resulting thymidine monoamine 5 was reacted with the methyl-carboxy bipyridine 3 in the presence of BOP and N-methymorpholine to form the thymidine methylbipyridyl 6 followed by treatment with tetra-butyl ammonium fluoride. The 3' hydroxyl of the thymidine methylbipyridyl 6 is exposed to succinic anhydride. The resulting 3' hemisuccinate is then reacted with aminopropyl CPG to form the CPG thymidine methylbipyridyl 7. The corresponding solid phase luminescent metal ion complex 8 may then be formed by reacting the CPG thymidine methylbipyridyl 7 with ruthenium bipyridinyl chloride. The solid phase luminescent metal ion complex 8 is then cleaved off the resin with a deprotecting agent to form the corresponding solution phase luminescent metal ion complex 9. Alternatively, an oligonucleotide is added to 8 to form the solid phase nucleic acid luminescent metal ion complex 9. Finally, 9 is cleaved off the resin with a deprotecting agent to form the corresponding solution phase oligonucleotide luminescent metal ion complex 11. The abbreviation "ODN," in scheme 2 refers to an oligodeoxynucleotide.

Scheme 2

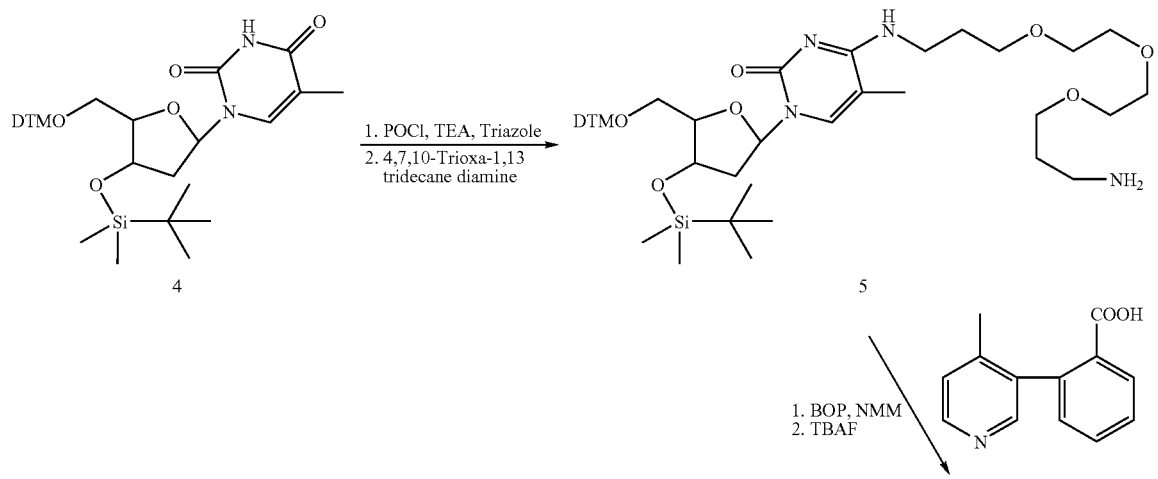

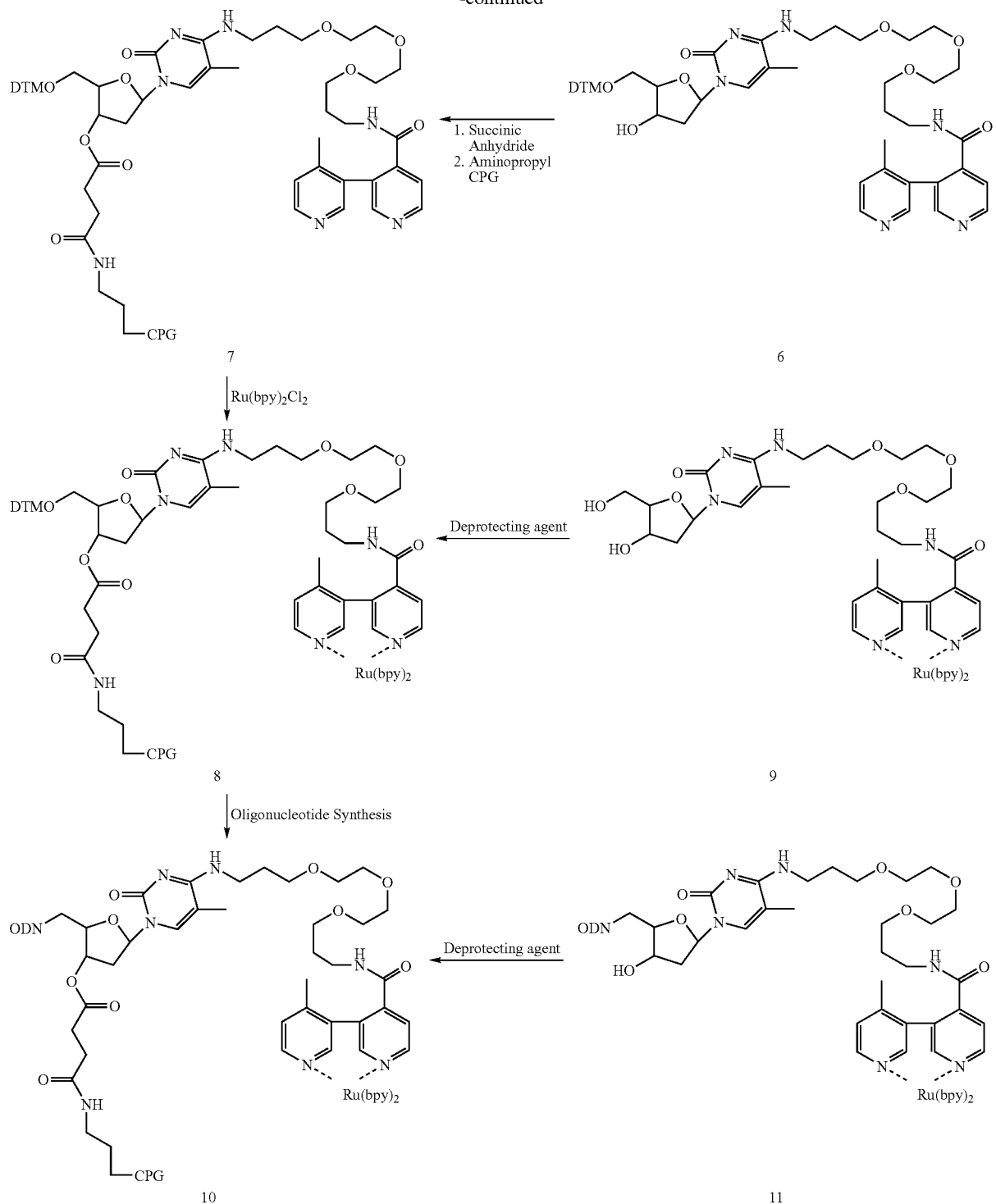

The above-recited synthetic schemes are intended to be exemplary of one embodiment of the invention, those of skill in the art will recognize that many other synthetic strategies employing metal ion chelating analogues are available. For example, the free amine in 5 may be substituted with other nucleophilic groups such as a sulfhydryl or hydroxyl with corresponding changes to the nucleophilic reactive group in 3. In addition, methods of covalently bonding a nucleic acid to a solid support are well known in the art and may be substituted into the above exemplary schemes.

By a slight modification of the method above, substituted or unsubstituted bipyridyl, substituted or unsubstituted phenanthroline, substituted or unsubstituted 2,4 pentanediene, substituted or unsubstituted hydroxamate, substituted or unsubstituted terpyridine, substituted or unsubstituted dipyridophenazine, or substituted or unsubstituted acetylacetonate may be incorporated into the resulting luminescent metal ion complex in place of the methylbipyridyl or unsubstituted bipyridyl exemplified in the above scheme (see Examples section; Bashkin et al., *J. Org. Chem.*, 61: 2314-2321 (1996); Ciana et al., *J. Org. Chem.*, 54: 1731-1735 (1996)).

In addition, the exemplary scheme is easily altered to allow for modification of a free amino group on a peptide to form a peptide luminescent metal ion complex. One of skill in the art will also immediately recognize that the exemplary scheme is easily adapted to other natural and non-natural nucleic acid nitrogenous bases such as guanine, cytosine, adenine, and uracil. In addition, one of skill in the art will immediately recognize that various solid supports may be used, such as polystyrene based supports and controlled pore glass based supports. Furthermore, it is well known that ruthenium is easily substituted with other metal ions, such as osmium and rhenium (see Hurley et al., *J. Am. Chem. Soc.*, 124 3749-3762 (2002)).

Solid phase oligonucleotide synthesis well known in the art. The above exemplary scheme is easily adapted to append a wide variety of oligonucleotide chains to the 5' of the 3' nucleic acid comprising the bidentate component of a luminescent metal ion complex. See Examples 1-5 below for additional exemplary syntheses.

Methods

The present invention provides methods of making a family of nucleic acid metal ion coordinating components and luminescent metal ion complexes. The methods include making solid phase and solution phase components and complexes.

Surprisingly, it has been discovered that nucleic acid metal ion coordinating components and nucleic acid luminescent metal ion complexes can be efficiently and inexpensively produced by covalently bonding to a solid support a nucleobase containing a metal ion chelating moiety attached to the nucleobase nitrogenous base. The method avoids the use of costly and inefficient phosphoramidites containing metal ion chelating moieties. The method also avoids blocking the 2'C of the deoxyribose or ribose sugar.

In an exemplary embodiment, the methods include the step of covalently bonding a first nucleobase to a non-nucleic acid spacer. The first nucleobase includes a nitrogenous base. The nitrogenous base has a linker covalently bonded to a first metal ion coordinating moiety. The non-nucleic acid spacer is covalently bound to a solid support. Additional nucleobases may be added sequentially to the to the 5' end of the first nucleobase to form a solid support bound nucleic acid having 2 to 100 nucleobases. The additional nucleobases may contain metal ion binding moieties attached to the nitrogenous base, the 2'C, or to the 5'C (either directly bonded to the 5'C or indirectly attached through a phosphodiester linkage or phosphodiester derivative linkage).

As discussed above, multiple luminescent metal ion complexes may be formed on a single carrier molecule, such as a nucleic acid. In an exemplary embodiment, additional multiple luminescent metal ion complexes are added to a nucleic acid metal ion complex after nucleic acid synthesis. In a related embodiment, additional multiple luminescent metal ion complexes are added by a method including covalently bonding a metal ion coordinating moiety to an available amine on a nitrogenous base.

The resulting solid support bound nucleic acid coordinating component may be cleaved from the solid support to yield the solution phase nucleic acid coordinating component. The desired metal ion and, optionally, one or more additional metal ion coordinating components may then be added to form a solution phase nucleic acid luminescent metal ion complex. Alternatively, the desired metal ion and, optionally, one or more additional metal ion coordinating components may be added to form a solid phase nucleic acid luminescent metal ion complex. The solid phase nucleic acid luminescent metal ion complex may then be cleaved from the solid support with a cleaving agent (discussed above) to form a solution phase nucleic acid luminescent metal ion complex. In a related embodiment, two additional metal ion coordinating components are added to the solution phase nucleic acid coordinating component or the solid phase nucleic acid coordinating component. Thus, in a related embodiment, the method includes the step of adding a second metal ion coordinating component, a third metal ion coordinating component, and a metal ion to form either a solution phase or a solid phase nucleic acid luminescent metal ion complex.

Typically, the methods include making a metal ion chelating probe having a metal ion coordinating component with a metal ion coordinating moiety covalently attached to a carrier molecule. The carrier molecule may be a polypeptide, nucleic acid, sugar, oligosaccharides, liposome, fatty acid, phospholipid, triacyl glycerol, steroid, or combinations thereof. In another exemplary embodiment, the carrier molecule is a single amino acid, a nucleobase, or a single carbohydrate monomer.

In another exemplary embodiment, methods of making a dual labeled probe is provided. Dual labeled probes are discussed in detail below. Methods of making a dual labeled probe include the step of covalently attaching a second label to the solid phase nucleic acid coordinating component or the solid phase nucleic acid luminescent metal ion complex produced by the methods described above. In an exemplary embodiment, the second label is an excited state energy quencher. Modes of quenching excited state energy are well known in the art and include, for example, electron transfer and energy transfer (e.g. dipole-dipole and collisional quenching).

Cleaving reagents are well known in the art of solid phase chemistry. Known cleaving reagents encompass the full range of acid and base compounds. One skilled in the art would recognize that a broad range of cleaving reagents are useful in the present invention. In an exemplary embodiment, the cleaving reagent is a mild acid, such as trifluoroacetic acid. In another exemplary embodiment, the cleaving reagent is ammonium hydroxide.

In another exemplary embodiment, the nucleic acids containing multiple luminescent metal ion complexes are synthesized enzymatically using a nucleic acid polymerase and triphosphate nucelobases covalently bonded to a luminescent metal ion complex.

Dual Labeled Probes

In another aspect, the present invention provides a family of dual labeled probes having a first label covalently attached to a carrier molecule and a second label covalently attached to the carrier molecule. Typically, the first label is an energy donor moiety and the second label is an energy acceptor moiety.

Labels are well known in the art. One of skill in the art will immediately recognize that a variety of labels are useful in the current invention. Labels useful in the current invention include but are not limited to, spectroscopic, chromatographic, paramagnetic, radioactive, fluorescent and energy quenching labels.

In an exemplary embodiment, the first label is a luminescent metal ion complex. Luminescent metal ion complexes are described in detail above. Thus, the luminescent metal ion complexes of a dual labeled probe typically include a metal ion coordinating moiety covalently bonded to a carrier molecule. The metal ion coordinating moiety is coordinated to a metal ion to produce a luminescent metal ion complex.

The second label is typically a quencher of excited state energy. A wide range of excited state energy quenchers can be used in conjunction with the luminescent metal ion complex of the current invention. Modes of emitting excited state energy are well known in the art and include, for example, electron transfer and energy transfer (e.g. dipole-dipole and collisional quenching). See, for example, Cardullo et al., Proc. Natl. Acad. Sci. USA 85: 8790-8794 (1988); Dexter, D. L., J. of Chemical Physics 21: 836-850 (1953); Hochstrasser et al., Biophysical Chemistry 45: 133-141 (1992); Selvin, P., Methods in Enzymology 246: 300-334 (1995); Steinberg, I. Ann. Rev. Biochem., 40: 83-114 (1971); Stryer, L. Ann. Rev. Biochem., 47: 819-846 (1978); Wang et al., Tetrahedron Letters 31: 6493-6496 (1990); Wang et al., Anal. Chem. 67: 1197-1203 (1995). Many mechanisms of excited state energy quenching are well known in the art, such as Dexter mechanism quenching and static quenching. The present invention is not limited by any particular quenching mechanism.

A non-limiting list of exemplary quenchers that can be used in conjunction with the luminescent metal ion complexes of the current invention is provided in Table 1.

TABLE 1

Suitable Labels for
Dual Labeled Probes 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
    coumarin
        7-amino-4-methylcoumarin (AMC, Coumarin 120)
        7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline TABLE 1-continued Suitable Labels for
Dual Labeled Probes Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
    sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives and other lanthanides (e.g., Eu, Dy, Sm)
squaraine dyes and derivatives
black hole quenchers
Alexa Dyes There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); Lakowicz, J., PRINCIPLES OF FLUORESCENCE CHEMISTRY, 2nd Ed., Plenum Press, New York (1999), and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a carrier molecule such as an oligonucleotide, as exemplified by the following references: Haugland (supra); Ullman et al., U.S. Pat. No. 3,996,345; Khanna et al., U.S. Pat. No. 4,351,760.

In an exemplary embodiment, the second label is a fluorophore capable of quenching excited energy from the donor label. In an exemplary embodiment, quencher molecules are fluorescent organic dyes derivatized for attachment to the carrier molecule, such as the terminal 3'-carbon or terminal 5'-carbon of a nucleic acid via a linking moiety. Linkers useful in covalently attaching a metal ion coordinating component to a carrier molecule are described in detail above. The linkers useful in covalently attaching a metal ion coordinating component to a carrier molecule are equally useful in covalently attaching a quencher of excited state to a carrier molecule. The properties of the attached label may be is modulated using linkers. Properties that are usefully controlled include, for example, hydrophobicity, hydrophilicity, surface-activity, the distance between donor and/or acceptor label pairs from the other carrier molecule component (e.g., carrier molecule) and the distance of the donor from the acceptor.

In certain embodiments, the linker provides flexibility and distance from the carrier molecule. In an exemplary embodiment, the linker serves to distance the quencher from a carrier molecule. Linkers with this characteristic have several uses. For example, a quencher held too closely to the carrier molecule may not interact with the donor group, or it may interact with too low of an affinity. When a quencher is itself sterically demanding, the interaction leading to quenching can be undesirably weakened, or it may not occur at all, due to a sterically-induced hindering of the approach of the two components.

Generally, it is preferred that an absorption band of the quencher substantially overlap the fluorescent emission band of the donor.

When the donor luminescent metal ion complex of the current invention utilizes fluorescence resonance energy transfer (FRET), the luminescent metal ion complex (donor) and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods described herein and known in the art.

The efficiency of FRET between the donor-acceptor pair can also be adjusted by changing ability of the two fluorescent proteins to dimerize or closely associate. If the donor and acceptor labels are known or determined to closely associate, an increase or decrease in association can be promoted by adjusting the distance between the two labels. Alternatively, the association between the donor-acceptor pair can be increased by, for example, utilizing a donor bearing an overall positive charge and an acceptor with an overall negative charge.

The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated.

In a exemplary embodiment, the quencher molecule is a fluorescein dye (FAM). Where the carrier molecule is a nucleic acid, the fluorescein moiety is preferably attached to the 5'-terminus of the oligonucleotide. In other embodiments, utilizing different donor groups, these groups are preferably introduced using an amidite derivative of the reporter group. Alternatively, reporter groups comprising reactive groups (e.g., isothiocyanates, active esters, etc.) can be introduced via reaction with a reactive moiety on a tether or linker arm attached to the oligonucleotide (e.g., hexyl amine).

In another exemplary embodiment, the quencher moiety is derived from TAMRA (tetramethylrhodamine carboxylic acid).

In another exemplary embodiment, the quencher moiety is derived from squaraine. An exemplary energy transfer from an nucleic acid luminescent Ru complex to squaraine is provided in the Examples section below.

In another preferred embodiment, the quencher moiety is a black hole quencher (also referred to herein as "BHQ") (see Cook, R., copending and commonly assigned U.S. patent application Ser. No. 09/567,863 filed May 9, 2000, which is herein incorporated by reference in its entirety for all purposes).

Means of detecting luminescent labels are well known to those of skill in the art. Thus, for example, fluorescent labels can be detected by exciting the fluorophore with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. The present invention is also used in conjunction with gated detection such as to minimize autofluorescence and/or scatter.

As discussed above, multiple luminescent metal ion complexes may be formed on a single carrier molecule to increase the detectable signal intensity while minimizing self-quenching. Although the detectable signal intensity is increased, it has been found that a single black hole quencher is capable of quenching multiple luminescent metal ion complexes.

In an exemplary embodiment, the dual labeled probe has the formula:

$$Q\text{-}Z\text{—}U \qquad (XVI)$$

In Formula (XVI), Q represents a quencher moiety. Z is a member selected from a bond and a carrier molecule. U is a luminescent metal ion complex comprising a metal ion and a metal ion coordinating moiety covalently attached to the carrier molecule Z. In a related embodiment, the metal ion coordinating moiety of U is covalently attached to the carrier molecule Z through a linker. In another exemplary embodiment, the quencher of excited energy state is covalently attached to the carrier molecule Z through a linker.

Thus, in an a related embodiment, the dual labeled has the formula:

$$Q\text{-}L'\text{-}Z\text{-}L''\text{-}U \qquad (XVII)$$

In Formula (XVII), Q is a quencher moiety, Z is selected from a bond and a carrier molecule, U is a luminescent metal ion complex, and L' and L" are independently linker molecules. The scope of the family of linkers represented by the symbol L described above is equally applicable here to the linkers represented by the symbols L' and L".

The carrier molecule may further comprise additional quencher moieties. In an exemplary embodiment, the number of additional quencher molecules is between 1 and 50. In another exemplary embodiment, the number of additional quencher molecules is between 1 and 10. In another exemplary embodiment, the number of additional quencher molecules is between 1 and 5. In another exemplary embodiment, the number of additional quencher molecules is one. Likewise, the carrier molecule may further comprises additional luminescent metal ion complexes. In an exemplary embodiment, the number of additional luminescent metal ion complexes is between 1 and 50. In an exemplary embodiment, the number of additional luminescent metal ion complexes is between 1 and 10. In an exemplary embodiment, the number of additional luminescent metal ion complexes is between 1 and 5. In an exemplary embodiment, the number of additional luminescent metal ion complexes is 1.

As described above, metal ion coordinating moieties may be covalently attached to any appropriate portion of the carrier molecule. Similarly, the quencher of excited energy state may also be covalently attached to any appropriate portion of the carrier molecule using the methods described above for covalent attachment of metal ion coordinating moieties.

In an exemplary embodiment, the quencher moiety has a structure having at least three radicals selected from substituted or unsubstituted aryl, substituted or unsubstituted heteroaryl and combinations thereof. At least two of the residues are covalently linked via an exocyclic diazo bond. The quencher typically includes a reactive functional group providing a locus for conjugation of the quencher to a carrier molecule.

In another exemplary embodiment, the quencher moiety has substantially no native fluorescence, particularly near their absorbance maxima or near the absorbance maxima of the luminescent metal ion complex. The quencher moiety will preferably have an absorbance maximum of from about 400 nm to about 760 nm, and more preferably, of from about 500 nm to about 600 nm.

In another exemplary embodiment, the quencher moiety has a structure according to Formula (XVIII):

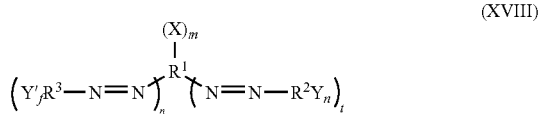

(XVIII)

wherein $R^1$, $R^2$ and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, and substituted or unsubstituted heteroaryl. X, Y and Y' are members independently selected from reactive functional groups; f is a number selected from 0 to 4, inclusive, such that when (f×s) is greater than 1, the Y' groups are the same or different; m is a number selected from 1 to 4, inclusive, such that when m is greater than 1, the X groups are the same or different; n is a number from 0 to 6, inclusive, such that when (n×t) is greater than 1, the Y groups are the same or different; s is a number from 0 to 6, inclusive, such that when s is greater than 1 the $R^3$ groups are the same or different; and t is a number from 1 to 6, inclusive, such that when t is greater than 1 the $R^2$ groups are the same or different, and when t is 1 and s is 0, a member selected from $R^1$, $R^2$ and combinations thereof is a member selected from substituted or unsubstituted polycyclic aryl and substituted or unsubstituted polycyclic heteroaryl groups.

In another exemplary embodiment, the quencher moiety has a structure according to Formula (XIX):

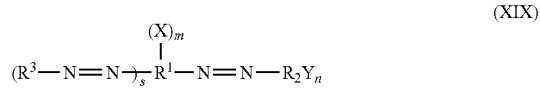

(XIX)

in which, X and Y are members independently selected from reactive functional groups; m is a number selected from 1 to 5, inclusive, such that when m is greater than 1, the X groups are the same or different; n is a number selected from 0 to 5, inclusive, such that when m is greater than 1, the Y groups are the same or different; s is a number selected from 1 to 5, inclusive, such that when s is greater than 1, the $R^3$ groups are the same or different. $R^1$, $R^2$, and $R^3$ are members independently selected from substituted or unsubstituted aryl, substituted or unsubstituted heteroaryl, and substituted or unsubstituted unsaturated alkyl, with the proviso that at least two of $R^1$, $R^2$ and $R^3$ are members independently selected from substituted or unsubstituted aryl, and substituted or unsubstituted heteroaryl.

In a preferred embodiment, m is 1; n is 0; c is 1; and $R^1$, $R^2$ and $R^3$ are members independently selected from aryl and substituted aryl.

In a preferred embodiment of each of the above-described aspects of the invention, $R^1$, $R^2$ and $R^3$ are members independently selected from aryl and aryl substituted with a member selected from amino, amino derivatives, nitro, $C_1$-$C_6$ alkyl, $C_1$-$C_6$ alkoxy and combinations thereof, and still more preferably, $R^1$ includes a structure according to Formula (XX):

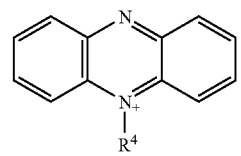

(XX)

wherein $R^4$ is a member selected from alkyl, substituted alkyl, aryl, substituted aryl, heteroaryl and substituted heteroaryl.

In another exemplary embodiment, the quencher moiety has a structure according to Formula (XXI):

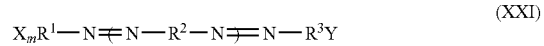

(XXI)

in which, X and Y are members independently selected from reactive functional groups; m is a number selected from 0 to 4, inclusive, such that when m is greater than 1, the X groups are the same or different; c is a number selected from 0 to 4, inclusive, such that when c is greater than 1, the $R^3$ groups are the same or different; v is a number from 1 to 10, inclusive, more preferably from 1 to 6, inclusive and more preferably still between 2 and 4, inclusive. When v is greater than one the $R^2$ groups are the same or different. $R^1$, $R^2$, and $R^3$ are members independently selected from substituted or unsubstituted aryl, substituted or unsubstituted heteroaryl and substituted or unsubstituted unsaturated alkyl, with the proviso that at least two of $R^1$, $R^2$ and $R^3$ are members selected from substituted or unsubstituted aryl, substituted or unsubstituted heteroaryl and combinations thereof.

In another exemplary embodiment, the quencher moiety has a structure according to Formula (XXII):

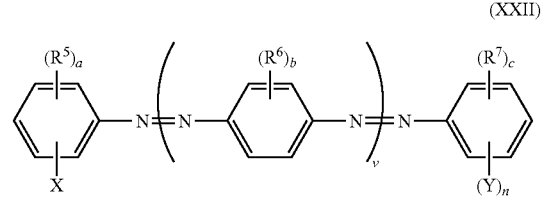

(XXII)

wherein, $R^5$, $R^6$ and $R^7$ are members independently selected from —NR'R", substituted or unsubstituted aryl, nitro, substituted or unsubstituted $C_1$-$C_6$ alkyl, and substituted or unsubstituted $C_1$-$C_6$ alkoxy, wherein R' and R" are independently selected from H and substituted or unsubstituted $C_1$-$C_6$ alkyl. X and Y are independently selected from the group consisting of reactive functional groups; n is a number from 0 to 1, inclusive; a is a number from 0 to 4, inclusive, such that when a is greater than 1, the $R^5$ groups are the same or different; b is a number from 0 to 4, inclusive, such that when (v×b) is greater than 1, the $R^6$ groups are the same or different; c is a number from 0 to 5, inclusive, such that when c is greater than 1, the $R^7$ groups are the same or different; and v is a number from 1 to 10, inclusive, such that when v is greater than 1, the value of b on each of the v phenyl rings is the same or different.

In another exemplary embodiment, the quencher moiety has a structure according to Formula (XXIII):

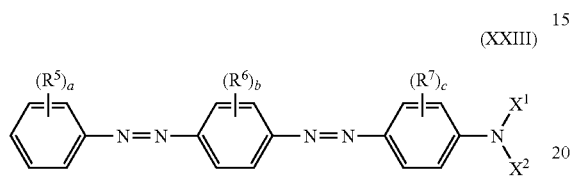

(XXIII)

wherein, $R^5$, $R^6$ and $R^7$ are members independently selected from amine, alkyl amine, substituted or unsubstituted aryl, nitro, substituted or unsubstituted $C_1$-$C_6$ alkyl, substituted or unsubstituted $C_1$-$C_6$ alkoxy; a is a number between 0 and 5, inclusive, such that when a is greater than 1, the $R^5$ groups are the same or different; b is a number between 0 and 4, inclusive, such that when b is greater than 1, the $R^6$ groups are the same or different; c is a number between 0 and 4, inclusive, such that when c is greater than 1, the $R^7$ groups are the same or different; and $X^1$ and $X^2$ are members independently selected from $C_1$-$C_6$ alkyl or $C_1$-$C_6$ substituted alkyl, —OH, —COOH, —NR'R", —SH, —OP(OX³)(N(R'R")₂, in which R' and R" are members independently selected from the group consisting of H, and alkyl or substituted alkyl.

In another exemplary embodiment, the quencher moiety has a structure according to a structure, which is a member selected from:

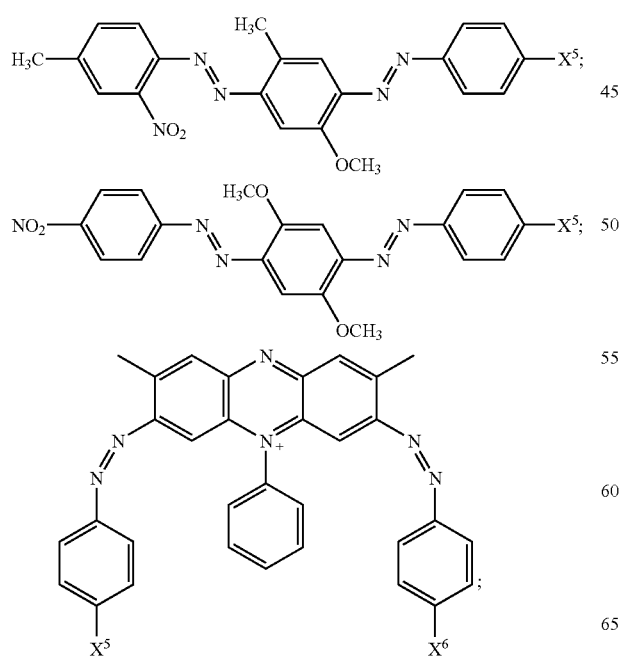

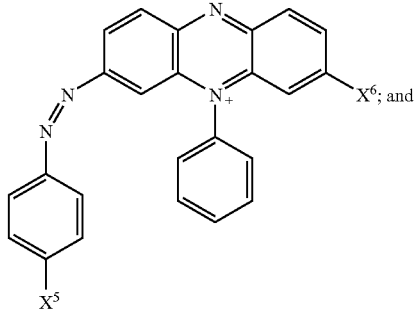

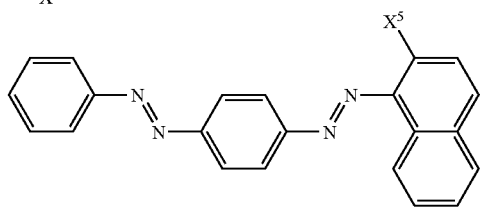

wherein $X^5$ and $X^6$ are members independently selected from H, substituted or unsubstituted $C_1$-$C_6$ alkyl, —OR', —COOR', —NR'R", —SH, —OP(OX³)(N(X⁴)₂, in which R' and R" are members independently selected from the group consisting of H, and alkyl or substituted alkyl. At least one of $X^5$ and $X^6$ is a reactive functional group. $X^3$ and $X^4$ are members independently selected from CN, and substituted or unsubstituted $C_1$-$C_6$ alkyl.

The following discussion is generally relevant to the identity of the reactive groups of the compounds of the invention and is particularly relevant to the groups X, $X^1$ and $X^2$ in each of the above-described aspects of the invention.

In a preferred embodiment, X is a member selected from amine, alkyl amine, substituted alkyl amine, and aryl amine groups, more preferably X has a structure according to Formula (XXIV):

(XXIV)

wherein, $R^9$ and $R^{10}$ are members independently selected from alkyl and substituted alkyl; and $X^1$ and $X^2$ are members independently selected from —CH₃, —OH, —COOH, —NH₂, —SH, —OP(OX³)(N(X⁴)₂)₂ wherein, $X^3$ and $X^4$ are members independently selected from alkyl and substituted alkyl, and preferably $X^3$ is cyanoethyl; and $X^4$ is isopropyl.

In another preferred embodiment, a member selected from $R^9$, $R^{10}$ and combinations thereof comprises a polyether. Preferred polyethers include, for example, poly(ethylene glycol), poly(propyleneglycol) and copolymers thereof.

In a further preferred embodiment, X has a structure according to Formula (XXV):

(XXV)

wherein, $X^1$, $X^2$, $X^3$ and $X^4$ are substantially as described above and p and q are numbers independently selected from 1 to 20, inclusive, preferably from 2 to 16, inclusive.

The compounds of the invention can be prepared as a single isomer or a mixture of isomers, including, for example cis-isomers, trans-isomers, diastereomers and stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single isomer. Techniques for inverting or leaving unchanged a particular stereocenter, and those for resolving mixtures of stereoisomers are well known in the art and it is well within the ability of one of skill in the art to choose an appropriate resolution or synthetic method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

Nucleic Acid Probes

The nucleic acid probes of the present invention are useful in detecting any target analyte (defined above). The nucleic acid probes of the present invention include a detector oligonucleotide covalently bonded to a metal ion coordinating component of a luminescent metal ion complex. Thus, the probes of the current invention may be immobilized on a solid support (such as a biochip) or free in solution. In some embodiments, the nucleic acid probes further comprise a second label to from a nucleic acid dual labeled probe. Applicable features of dual labeled probes are discussed in detail above.

Detector oligonucleotides are oligonucleotides capable of binding to a target analyte. Mechanisms of oligonucleotide binding are well known in the art. The detector oligonucleotide may bind to a target analyte using any applicable binding mechanism, such as hydrogen bonding, ionic interactions, covalent bonding, Van der Waals forces, dipole-dipole interactions, hydrophobic interactions, base stacking or pi-pi interactions, and the like. Where the target analyte is a polypeptide, such as an oligonucleotide binding protein, the detector oligonucleotide will typically bind to the polypeptide using a combination of binding mechanisms. Where the target analyte is a nucleic acid, the detector oligonucleotide will typically hybridize primarily through hydrogen bonding interactions.

Luminescent metal ion complexes of the invention are useful in conjunction with nucleic-acid probes and can be used as components of detection agents in a variety of techniques involving fluorescence, fluorescence polarization, electrochemiluminescence, gated detection, electrochemistry, and electrochemical sequence evaluation. In addition, luminescent metal ion complexes of the invention are useful as components in DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the luminescent metal ion complexes can be used in probes of substantially any format, including, for example, a format selected from molecular beacons, scorpion probes, sunrise probes, conformationally assisted probes, light up probes, invader probes, and TaqMan™ probes.

Thus, in another aspect, the present invention provides methods for detecting a target analyte using a nucleic acid probe. The method includes contacting the target analyte with a nucleic acid probe. The nucleic acid probe includes a detector oligonucleotide covalently bonded to a metal ion coordinating component of a luminescent metal ion complex. The target analyte is allowed to bind to the detector oligonucleotide to form a target analyte-detector oligonucleotide complex. The presence of the target analyte-detector oligonucleotide complex is confirmed by detecting a detectable signal produced by the luminescent metal ion complex of the detector oligonucleotide. The detectable signal is typically produced by allowing the luminescent metal ion complex to absorb energy to produce an excited state luminescent metal ion complex. The excited state luminescent metal ion complex thereafter emits the excited state energy in a detectable form. In an exemplary embodiment, the detectable excited state energy emission is light.

A variety of energy sources are useful in producing an excited state luminescent metal ion complex, including light, electrical potential, electron transfer or chemical reaction. In addition, light detection methods are well known in the art and include, for example, visual fluorescence detection by means of photographic film, by the use of electronic detectors such as charge coupled devices (CCDs) or photomultipliers and the like. In a related embodiment, the detectable signal is detected using fluorescence polarization.

An alternative detection scheme, which is theoretically more sensitive than autoradiography, is time-resolved fluorimetry. According to this method, pulsed or modulated excitation combined with a gated or frequency modulated detection system is used to detect a luminescent metal ion complex of the current invention with a long radiative lifetime attached to a molecule of interest, such as a nucleic acid or polypeptide.

In an exemplary embodiment, the labeled probe includes a luminescent metal ion complex with a long radiative lifetime and a fluorophore with a shorter radiative lifetime than the luminescent metal ion complex. In a related embodiment, the radiative lifetime of the luminescent metal ion complex is on the microsecond timescale. In another related embodiment, the radiative lifetime of the luminescent metal ion complex is greater than 50 ns. In another related embodiment, the radiative lifetime of the luminescent metal ion complex is greater than 100 ns. In another related embodiment, the radiative lifetime of the luminescent metal ion complex is greater than 500 ns. In another related embodiment, the radiative lifetime of the luminescent metal ion complex is greater than 900 ns. Where the luminescent metal ion complex is sufficiently close to the fluorophore, the radiative lifetime of the fluorophore is extended. As the distance between the fluorophore and the luminescent metal ion complex decreases, the radiative lifetime of the fluorophore approaches the radiative lifetime of the luminescent metal ion complex. Thus, not only can the presence of the fluorophore and/or luminescent metal ion complex be detected, but the distance between the fluorophore and/or luminescent metal ion complex may also be measured. Therefore, a luminescent metal ion complex with a long radiative lifetime may be used in conjunction with a fluorophore with a short radiative lifetime to measure distances between point on a carrier molecule, such as a nucleic acid or a polypeptide. Alternatively, intermolecular distances may be measured with a luminescent metal ion complex covalently bound to a carrier molecule and a fluorophore bound to a target analyte. Also, gated detection can be used to selectively detect fluorophores that have been sensitized (have received energy and are therefore in proximity) by a luminescent metal ion complex. In a related embodiment, the quencher includes absorbers of long wavelength light, such as BODIPY, squaraines, Cy5, Cy5.5 and alexa dyes. In a further related embodiment, the quencher absorbs light at wavelengths greater than 580 nm.

In an exemplary embodiment, the nucleic acid probe is bound to a solid support, such as a biochip.

In another exemplary embodiment, the nucleic acid probe is free in solution. In this embodiment, the target molecule-detector oligonucleotide complex is separated from the reaction solution. In a related embodiment, the reaction solution is separated from the target analyte-detector oligonucleotide complex using a chromatographic column. Chromatographic columns are well known in the art and include, but are not limited to, size exclusion columns, ion exchange columns, and hydrophobic columns.

In another exemplary embodiment, the nucleic acid probe further comprises a quencher moiety to form a nucleic acid dual labeled probes. The characteristics of dual labeled probes discussed above are equally applicable to the nucleic acid dual labeled probes. In a further related embodiment, the detector oligonucleotide is a stem loop structure as described in Tyagi et al., U.S. Pat. No. 5,925,517, which is herein incorporated by reference in its entirety for all purposes. In a related embodiment, the detector oligonucleotide stem loop structure contains a quencher, preferably a BHQ, covalently bound to the 5' end and a metal ion coordinating component covalently bound to the 3' end. The target analyte preferably contains a nucleic acid target sequence to which a portion of the stem loop is capable of hybridizing. The metal ion coordinating component forms a portion of a luminescent metal ion complex. As described above, the detector oligonucleotide stem loop may contain additional quencher moieties and/or metal ion complexes attached at any applicable position. Exemplary nucleic acid probes containing detector oligonucleotides and stem loop structures are presented in the Examples section below.

In another exemplary embodiment, a voltage is applied to the target sequence-detector oligonucleotide complex using an electrode, wherein the detector oligonucleotide and/or the target nucleotide portion of the of the target sequence-detector oligonucleotide complex is immobilized on the electrode.

In another exemplary embodiment, target sequence-detector oligonucleotide complex is visualized using electrochemiluminescence. The method includes: (a) contacting the target sequence with the nucleic acid probe; (b) binding the target sequence to the detector oligonucleotide of the nucleic acid probe to form a target sequence-detector oligonucleotide complex; (c) adding a coreactant to the target analyte-detector oligonucleotide complex; (d) applying a voltage to the target sequence-detector oligonucleotide complex to oxidize the coreactant and target analyte-detector oligonucleotide complex; (e) detecting the emitted light; and (f) returning the target analyte-detector oligonucleotide complex to its original oxidation state for another oxidation-emission cycle. In a further related embodiment, the coreactant is an amine (e.g. tripropylamine). In a related embodiment, the voltage is applied to the target sequence-detector oligonucleotide complex using an electrode, wherein the detector oligonucleotide and/or the target nucleotide portion of the of the target sequence-detector oligonucleotide complex is immobilized on the electrode.

In another exemplary embodiment, the present invention provides a method for detecting a nucleic acid target sequence using electrochemical detection. The method includes: (a) contacting the target sequence with the nucleic acid probe; (b) binding the target sequence to the detector oligonucleotide of the nucleic acid probe to form a target sequence-detector oligonucleotide complex; (c) applying an electrical voltage to the target sequence-detector oligonucleotide complex to oxidize the detector oligonucleotide portion of the target sequence-detector oligonucleotide complex; and (g) returning the detector oligonucleotide portion of the target analyte-detector oligonucleotide complex to its original oxidation state. In a related embodiment, the detector oligonucleotide portion of the target sequence-detector oligonucleotide complex is reduced back to its original oxidation state by abstracting an electron from the target sequence portion. In a further related embodiment, the electron is abstracted from a guanine of the target sequence.

In another aspect, the present invention provides a method for evaluating the sequence in an oligonucleotide target sequence. The method includes: (a) contacting the target sequence with a nucleic acid probe having a detector oligonucleotide; (b) binding the target sequence to the detector oligonucleotide portion of the nucleic acid probe to form a target sequence-detector oligonucleotide complex; (c) applying a voltage to the target sequence-detector oligonucleotide complex; and (d) detecting the voltage flowing through the target sequence-detector oligonucleotide complex.

In another aspect, the presence of a nucleic acid target sequence is detected by: (a) contacting the target sequence with the nucleic acid probe; (b) binding the target sequence to the detector oligonucleotide of the nucleic acid probe, thereby altering the conformation of the detector oligonucleotide, causing a change in a fluorescence parameter; and (c) detecting the change in the fluorescence parameter, thereby detecting the target sequence.

In another aspect, the invention provides another method for detecting the presence of a nucleic acid target sequence. The method includes: (a) hybridizing to the target sequence a detector oligonucleotide comprising a single-stranded target binding sequence and an intramolecularly associated secondary structure 5' to the target binding sequence, wherein at least a portion of the target sequence forms a single stranded tail which is available for hybridization to the target sequence; (b) in a primer extension reaction, synthesizing a complementary strand using the intramolecularly associated secondary structure as a template, thereby dissociating the intramolecularly associated secondary structure and producing a change in a fluorescence parameter; and (c) detecting the change in the fluorescence parameter, thereby detecting the nucleic acid target sequence.

In another aspect, the invention provides a method for detecting amplification of a target sequence. The method includes the use of an amplification reaction including the following steps: (a) hybridizing the target sequence and the detector oligonucleotide of a nucleic acid probe, wherein the nucleic acid probe includes an intramolecularly associated secondary structure 5' to the detector oligonucleotide. At least a portion of the detector oligonucleotide sequence forms a single stranded tail which is available for hybridization to the target sequence; (b) extending the hybridized detector oligonucleotide with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In another aspect, the invention provides another method for detecting amplification of a target sequence. The method includes the use of an amplification reaction including the following steps: (a) hybridizing the target sequence and the detector oligonucleotide of a dual labeled nucleic acid probe; (b) digesting the dual labeled nucleic acid probe with nucleic acid polymerase and producing a change in a fluorescence parameter; and (c) detecting the change in the fluorescence parameter, thereby detecting the target sequence.

The target sequence is amplified by any method known in the art, including, for example, Strand Displacement Amplification, Polymerase Chain reaction 3SR, TMA and NASBA.

Where the detector and or target oligonucleotide is immobilized, the solid support may be a paramagnetic solid support. In an embodiment, the solid support bound detector or target oligonucleotide is bound to the target or detector molecule and separated from the reaction solution using a magnet or electromagnet.

The change in the fluorescence parameter may be facilitated by a detector oligonucleotide comprising a luminescent metal ion complex of the invention wherein the luminescent metal ion complex is nonfluorescent or weakly fluorescent in solution and emits a stronger fluorescent signal upon hybridization of the detector oligonucleotide with the target sequence.

In another exemplary embodiment, the change in the fluorescence parameter is facilitated by a detector oligonucleotide comprising luminescent metal ion complex of the invention and a quencher of excited state energy. Modes of quenching excited state energy are well known in the art and includes, for example, electron transfer and energy transfer (e.g. dipole-dipole and collisional quenching). The detector oligonucleotide is preferably in a conformation that allows fluorescence energy transfer between the luminescent complex and the quencher when the luminescent complex is excited. Furthermore, a change in fluorescence is detected as an indication of the presence of the target sequence, and that change in fluorescence is preferably detected in-real time. The detector oligonucleotide can assume substantially any intramolecularly associated secondary structure, but this structure is preferably a member selected from hairpins, stem-loop structures, pseudoknots, triple helices and conformationally assisted structures. Moreover, the intramolecularly base-paired secondary structure preferably comprises a portion of the target binding sequence. Moreover, the intramolecularly associated secondary structure, preferably includes a totally or partially single-stranded endonuclease recognition site. The complementary strand can be prepared by any art-recognized method for preparing such strands, but is preferably synthesized in a target amplification reaction, and more preferably by extension of the target sequence using the detector oligonucleotide as a template.

In addition to their general utility in species designed to probe nucleic acid amplification, detection and quantification, the present luminescent metal ion complexes can be used in substantially any nucleic acid probe format now known or later discovered. For example, the metal ion coordinating component of a luminescent metal ion complex or luminescent metal ion complex of the invention can be incorporated into probe motifs, such as Taqman probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature* Biotechnology 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. Pending application Ser. No. 09/591,185 filed Jun. 8, 2000), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)), invader probes (Brow et al., U.S. Pat. No. 6,001,567 (1999), Neri et al., U.S. Pat. No. 6,358,691 (2002), U.S. Pat. No. 6,355,437 (2002), U.S. Pat. No. 6,194,149 (2001), which are herein incorporated by references for all purposes) and the like. These and other probe motifs with which the present quenchers can be used are reviewed in NONISOTOPIC DNA PROBE TECHNIQUES, Kricka, L., Academic Press, Inc. 1992.

The detector oligonucleotides for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many art recognized references.

Preferably, the 3'-terminal nucleotide of the oligonucleotide probe is blocked or rendered incapable of extension by a nucleic acid polymerase. Such blocking is conveniently carried out by the attachment of a bidentate portion of a luminescent metal ion complex or a luminescent metal ion complex molecule to the terminal 3'-carbon of the oligonucleotide probe.

The detector oligonucleotide can comprise DNA, RNA or chimeric mixtures or derivatives or modified versions thereof. In addition to being labeled with a metal ion coordinating component of a luminescent metal ion complex, the oligonucleotide can be modified at the base moiety, sugar moiety, or phosphate backbone with other groups such as radioactive labels, minor groove binders, intercalating agents an the like.

Detector oligonucleotides can include one or more modified base moieties, modified sugar moieties, or phosphate backbone as described above.

Methods of making detector oligonucleotides are well known in the art and described above. Thus, oligonucleotide probes of the invention can be synthesized by a number of approaches, e.g., Ozaki et al., *Nucleic Acids Research,* 20: 5205-5214 (1992); Agrawal et al., *Nucleic Acids Research,* 18: 5419-5423 (1990); or the like. The oligonucleotide probes of the invention are conveniently synthesized on an automated DNA synthesizer, e.g., a P.E. Biosystems, Inc. (Foster City, Calif.) model 392 or 394 DNA/RNA Synthesizer, using standard chemistries, such as phosphoramidite chemistry (see, for example, disclosed in the following references: Beaucage et al., *Tetrahedron,* 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458, 066; and 4,973,679). Alternative chemistries resulting in non-natural backbone groups, such as phosphorothioate, phosphoramidite, and the like, may also be employed.

When the detector oligonucleotides are synthesized utilizing an automated DNA synthesizer, the stabilizing moiety, energy transfer donor and energy transfer acceptor moieties are preferably introduced during automated synthesis. Alternatively, one or more of these moieties can be introduced either before or after the automated synthesis procedure has commenced. In another exemplary embodiment, one or more of these moieties is introduced after the automated synthesis is complete.

Peptide Probes

Peptide probes of the present invention include peptides, polypeptides, proteins and peptide nucleic acids that are labeled with a metal ion coordinating component of a luminescent metal ion complex or a luminescent metal ion complex of the invention. The peptide probes can be used in both in vivo and in vitro enzymatic assays or protein binding essays. Peptide probes also include dual labeled peptide probes, which additionally contain a quencher of excited energy.

Thus, in another aspect the present invention provides a method for determining whether a sample contains a target protein, wherein the target protein is an enzyme or a binding protein. The method comprises: (a) contacting the sample with a peptide probe having a luminescent metal ion complex; (b) exciting the luminescent complex; and (c) determining a fluorescence property of the sample, wherein the presence of the target protein in the sample results in a change in the fluorescence property of the luminescent complex.

In a further aspect of the invention, the present invention provides a method for determining whether a sample contains a target analyte, wherein the method comprises: (a) contacting the sample with a peptide probe comprising luminescent metal ion complex; (b) forming a peptide probe-target analyte complex; (c) optionally separating the peptide probe-target analyte complex from the reaction solution; (d) exciting the luminescent complex; and (e) detecting the emitted photons.

In an exemplary embodiment, the reaction solution is separated from the peptide probe-target analyte complex using a chromatographic column. Chromatographic columns are well known in the art and include, but are not limited to, size exclusion columns, ion exchange columns, and hydrophobic columns.

In another aspect of the invention, the present invention provides a method for determining the presence of a target analyte, wherein the method comprises: (a) contacting the target analyte with a peptide probe; (b) forming a peptide probe-target analyte complex; (c) optionally separating the peptide probe-target analyte complex from the reaction solution; (d) adding a co-reactant to the peptide-target analyte complex; (d) applying a voltage to the peptide probe-target analyte complex to oxidize the co-reactant and peptide probe-target analyte complex; (e) detecting the emitted light from the oxidation reaction; and (g) returning the peptide probe-target analyte complex to its original oxidation state for another oxidation-emission cycle.

In an exemplary embodiment, the co-reactant is tripropylamine.

In an exemplary embodiment, the peptide probe comprises a metal ion coordinating component of a luminescent metal ion complex. In another exemplary embodiment the peptide probe comprises a luminescent metal ion complex.

In an exemplary embodiment, the voltage is applied to the peptide probe-target analyte complex using an electrode, wherein the peptide probe portion or the target analyte portion of the of the peptide probe-target analyte complex is immobilized on the electrode.

In an exemplary embodiment, the target analyte or the peptide probe is bound to a paramagnetic solid support.

The assay methods also can be used to determine whether a compound alters the activity of an enzyme, i.e., screening assays. Thus, in a further aspect, the invention provides methods of determining the amount of activity of an enzyme in a sample from an organism. The method includes: (a) contacting a sample comprising the enzyme and the compound with a peptide probe, wherein the peptide probe comprises luminescent metal ion complex; (b) forming a peptide-sample complex; (d) exciting the luminescent complex; and (e) determining a fluorescence property of the sample, wherein the activity of the enzyme in the sample results in a change in the fluorescence property.

In an exemplary embodiment, the fluorescence property is fluorescence polarization. The implementation of fluorescence polarization to the peptide probes here is analogous to the fluorescence polarization discussed above for oligonucleotide detectors.

In an exemplary embodiment, the change in the fluorescence property is facilitated by a peptide probe comprising luminescent metal ion complex, wherein the position of the peptide probe relative to the target analyte allows aromatic ring portions of the luminescent complex to stack between aromatic ring portions of the target analyte wherein the stacking changes the fluorescence property of the luminescent complex. In a related embodiment, the target analyte is a target protein.

In an exemplary embodiment, the change in the fluorescence property is facilitated by a peptide probe comprising luminescent metal ion complex of the invention and a quencher of excited state energy. The peptide probe is preferably in a conformation that allows fluorescence energy transfer between the luminescent complex and the quencher when the luminescent complex is excited. Furthermore, a change in fluorescence is detected as an indication of the presence of the analyte, and that change in fluorescence is preferably detected in-real time.

In an exemplary embodiment, the amount of enzyme activity in the sample is determined as a function of the degree of fluorescence resonance energy detected in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that effect the activity of proteases are natural subjects of combinatorial chemistry. Screening compounds produced by combinatorial chemistry requires convenient enzymatic assays.

In another aspect of the invention, the present invention provides a method for determining the presence of a target analyte, wherein the method comprises: (a) contacting the target analyte with a dual labeled peptide probe; (b) forming a dual labeled peptide probe-target analyte complex; (c) degrading the dual labeled peptide with a protease and producing a change in a fluorescence parameter; and (c) detecting the change in the fluorescence parameter, thereby detecting the presence of the target analyte.

Convenient assays for proteases are based on fluorescence measurement as outlined above. Proteolysis separates the fluorophore from the remainder of the peptide probe, resulting in a decrease in size of the peptide probe. The resulting attenuated peptide may be detected by chromatographic techniques or by fluorescence polarization, as outlined above. Existing protease assays use short peptide substrates incorporating unnatural chromophoric amino acids, assembled by solid phase peptide synthesis.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent protein moieties each linked by a randomized linker moiety can be generated using recombinant engineering techniques or synthetic chemistry techniques. Screening the members of the library can be accomplished by measuring a signal related to cleavage, such as fluorescence polarization, after contacting the cleavage enzyme with each of the library members of the tandem fluorescent protein construct.

When the cleavage agent of interest is a protease, the linker can comprise a peptide containing a cleavage recognition sequence for the protease. A cleavage recognition sequence for a protease is a specific amino acid sequence recognized by the protease during proteolysis cleavage. In particular, the linker can contain any of the amino acid sequences in TABLE I. The sites are recognized by the enzymes as indicated and the site of cleavage is marked by a hyphen. Other protease cleavage sites also are known in the art and can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Luminescent metal ion complexes of the invention are useful in conjunction with peptide probes and can be used as components of detection agents in a variety of techniques involving fluorescence, fluorescence polarization, electrochemiluminescence, gated detection, electrochemistry, and electrochemical sequence evaluation.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, any feature of the luminescent metal ion complexes described above can be incorporated into any of the methods or compositions (e.g., the dual labeled probes) without departing from the scope of the invention.

In addition, the patents and scientific references cited herein are incorporated by reference in their entirety for all purposes.

EXAMPLES

General Methods

DNA sequences were made with a Biosearch 8700 DNA synthesizer using standard phosphoramidite reagents. The Apo B sequence is 5'-d-CGA-GAA-TCA-CCC-TGC-CAG-ACT-TCC-GT-3'. The β-action sequence is 5'-ATG-CCC-TCC-CCC-ATG-CCA-TCC-TGC-G-3'. This sequence was added to the Ru(bpy)$_2$(mcbpy)-CPG. To make dual-labeled probes, BHQ2 amidite (Biosearch Technologies) was used. In samples with a 5' squaraine label, a carboxy squaraine dye was coupled to an amine that had been added via an MMT protected amino phosphoramidite. The squaraine-COOH and amino-labeled oligonucleotide were coupled using BOP while the oligonucleotide was still attached to solid support. All synthetic DNA samples were dual-HPLC purified by anion exchange (Dionex DNA Pac™ PA-100 column, solvent A: 0.038 M tris[hydroxymethyl]aminomethane, 15% acetonitrile, solvent B: solvent A with 1 M NaBr) followed by reversed-phase (Hamilton PRP-1 column, solvent A: 0.1 N TEAA, solvent B: acetonitrile). Sample purity was confirmed by analytical anion-exchange and reversed-phase HPLC.

All spectroscopic measurements were made in a buffer solution of 10 mM trizma hydrochloride, 50 mM KCl and 3.5 mM MgCl$_2$. Absorption spectra were recorded using a HP 8452 diode-array spectrophotometer. Additional absorption and fluorescence measurements were made using a S2000 Ocean Optics spectrometer with a CCD-array detector, PX-2 pulsed Xenon lamp and DT-1000 deuterium tungsten halogen light source. Additional fluorescence measurements were obtained with a Perkin Elmer LS50b luminescence spectrometer and a Molecular Devices SpectraMax Gemini spectrofluorometer.

Example 1

Example 1 illustrates a method of making solid phase nucleic acid luminescent metal ion complexes.

Example 1.1

Preparation of a Solution Phase Nucleic Acid Metal Ion Coordinating Component 6

A solution of 12 mL (20 g, 130 mmol) phosphorus oxychloride and 40 g (580 mmol) of 1,2,4 triazole in 400 mL of dry CH$_3$CN was chilled on ice to 0° under argon. Triethylamine, 90 mL (90 g, 900 mmol) was added slowly dropwise with stirring over ½ hr. Next, 31 g (47 mmol) of 5'-(4,4'dimethoxytrityl)-3'-O-tertbutyldimethysilyl thymidine 4 was dissolved in 200 mL dry CH$_3$CN and added slowly dropwise over ½ hr. The solution was stirred and allowed to warm to room temperature overnight. The solution was reduced to a gum under reduced pressure, and dissolved in 500 mL EtOAc. 300 mL saturated aqueous NaHCO$_3$ was added and the mixture was shaken and separated. The organic phase was washed with another 300 mL portion of saturated aqueous NaHCO$_3$ and then dried over MgSO$_4$, filtered and evaporated to give the N$^4$-triazolide as a brown foam. This material was dissolved in 150 mL of CH$_3$CN and added dropwise with stirring to a solution of 30 mL (31.4 g, 300 mmol) 4,7-10 trioxo-1,13 tridecane diamine in 300 mL CH$_3$CN which had been chilled to 0° on ice. The mixture was stirred overnight and allowed to warm to room temperature. The solution was reduced to a tar by rotary evaporation, then re-dissolved in 300 mL EtOAc. The solution was washed with 300 mL of saturated NaHCO$_3$ and dried over MgSO$_4$. Filtration, followed by reduction to a tar by rotary evaporation and high vacuum overnight gave 24.3 g of the N$^4$-(4,7-10 trioxo-1,13 tridecane diamine) adduct 5 as a foam. 10 g of this material was dissolved in a mixture of 200 mL dimethylformamide (DMF), 3.3 g of 1-carboxy-8-methyl bipyridine, 5 g of BOP and 3 mL of N-methymorpholine (which had been stirred for 3 hrs) and the solution was stirred for about 18 hrs. The solution was reduced to a tar by rotary evaporation. The residue was dissolved in 300 mL dichloromethane (DCM) and the organic phase was washed with 150 mL saturated NaHCO$_3$, then dried over MgSO$_4$ and filtered. High vacuum was applied overnight. The product was treated with a mixture of 300 mL tetrahydrofuran (THF), 60 mL 1 N tetra-butyl ammonium fluoride (TBAF) in THF and 10 mL of HOAc. After thorough mixing the solution was allowed to stand overnight. The mixture was then stripped to a tar and re-dissolved in 300 mL DCM. The solution was washed with 150 mL saturated NaHCO$_3$ and the organic phase dried over MgSO$_4$ The solution was filtered and reduced by rotary evaporation, then purified by column chromatography on a 5×20 cm bed of activated silica gel eluted with a gradient of 5-15% MeOH (all 1% pyridine) in DCM. Fractions were inspected by thin layer chromatography (TLC) in 10% MeOH, 1% pyridine in DCM and visualized with 10% H$_2$SO$_4$ and heat. Fractions containing pure product (rf 0.25, 10% MeOH and 2% pyridine in DCM) were pooled and reduced by rotary evaporation and high vacuum to yield 8 g of 6 as a white foam. $^1$H NMR ($\delta$ CDCl$_3$): 8.7 (d, 1H), 8.65 (s, 1H), 8.5 (d, 1H), 8.2 (s, 1H), 7.75 (dd, 1H), 7.7-7.6 (m, 4H), 7.4 (d, 2H), 7.3-7.1 (m, 12H), 6.8 (d, 4H), 6.4 (m, 1H), 5.9 (t, 1H), 4.5 (m, 1H), 4.1 (q, 1H), 3.7 (s, 6H), 3.6-3.5 (m, 16H), 3.4 (m, 4H), 3.3 (m, 1H) 3.0 (m, 1H) 2.6 (d, 2H), 2.5 (m, 1H), 2.4 (s, 3H), 2.2 (m, 1H), 1.9-1.7 (m, 6H), 1.5 (s, 3H).

Anal Calc'd for C$_{53}$H$_{62}$N$_6$O$_{10}$.MeOH: C, 66.46; H, 6.77, N, 8.62.

Found: C, 66.30; H, 6.95; N, 9.07.

Example 1.2

Preparation of a Solid Phase Nucleic Acid Metal Ion Coordinating Component 7

A hemisuccinate was made by first drying 2 g of 6 by rotary evaporation of the compound with 50 mL dry pyridine. Next, 1 g of succinic anhydride was added along 50 mL of dry pyridine and 100 microliters of N-methylimidazole. The mixture was shaken by hand until all solids dissolved. After 2 days, TLC (same mobile phase as above) showed conversion to a lower rf compound, (rf 0.15) The mixture was treated with 5 mL of MeOH and stripped to a tar. The crude mixture was re-dissolved in 200 mL of DCM and washed 3 times with 0.5 N KH$_2$PO$_4$. The organic phase was dried over MgSO$_4$ and evaporated to a tar which was used to functionalize the controlled pore glass (CPG).

A solution of 1 g of the resulting hemisuccinate in 50 mL of DMF was treated with 500 mg of BOP and 300 microliters of NMM. After 5 min, the solution was poured into a 250 mL erlenmeyer flask which contained 10 mL of 500 an aminopropyl CPG. The flask was stoppered and allowed to stand overnight. The slurry was poured into a 150 mL coarse frit sintered glass funnel atop a 1 L side arm flask. The support was then washed three times with 200 mL of CH$_2$Cl$_2$, twice with 100 mL of CH$_3$CN. Next, 100 ml of a mixture of acetic anhydride, N-methyl imidazole and THF (1:1:8) was added to the support. After 30 min exposure, the acetylation solution was removed and the support was washed three times with 100 mL of CH$_3$CN to form the solid phase nucleic acid metal ion coordinating component 7. A small amount of this was dried. The DMT loading was 48 μm/g (17). The derivatized CPG was dried under high vacuum overnight.

Example 1.3

Preparation of a Solid Phase Nucleic Acid Luminescent Metal Ion Complex 8

7 was refluxed for 5 hours with a molar excess (ca. tenfold) of Ru(bpy)$_2$Cl$_2$ (commercially available from Aldrich) in ethanol/water (2/3, v/v) to form the solid phase nucleic acid luminescent metal ion complex 8. After the reaction mixture has cooled, the CPG is collected by suction filtration and washed with ethanol.

Example 1.4

Preparation of a Solid Phase Nucleic Acid Luminescent Metal Ion Complex 10 Containing Various Oligonucleotide Sequences 8 was loaded onto a Biosearch 8700 DNA synthesizer and subjected to successive round of standard oligonucleotide synthesis using standard phosphoramidite reagents. The following sequences were synthesized: ApoB (to form the corresponding solid support bound 5'-ApoB-mdT(Ru(bpy)$_2$(mcbpy))-(CPG)), T$_9$ (to from the corresponding 5'-T$_9$-mdT(Ru(bpy)$_2$(mcbpy))-(CPG)), and β-Actin (5'-β-Actin-TT-mdT(Ru(bpy)$_2$(mcbpy))-(CPG) and 5'-β-Actin-mdT(Ru(bpy)$_2$(mcbpy))-(CPG)).

Example 1.5

Preparation of a Solution Phase Nucleic Acid Luminescent Metal Ion Complexes

Figure 2:
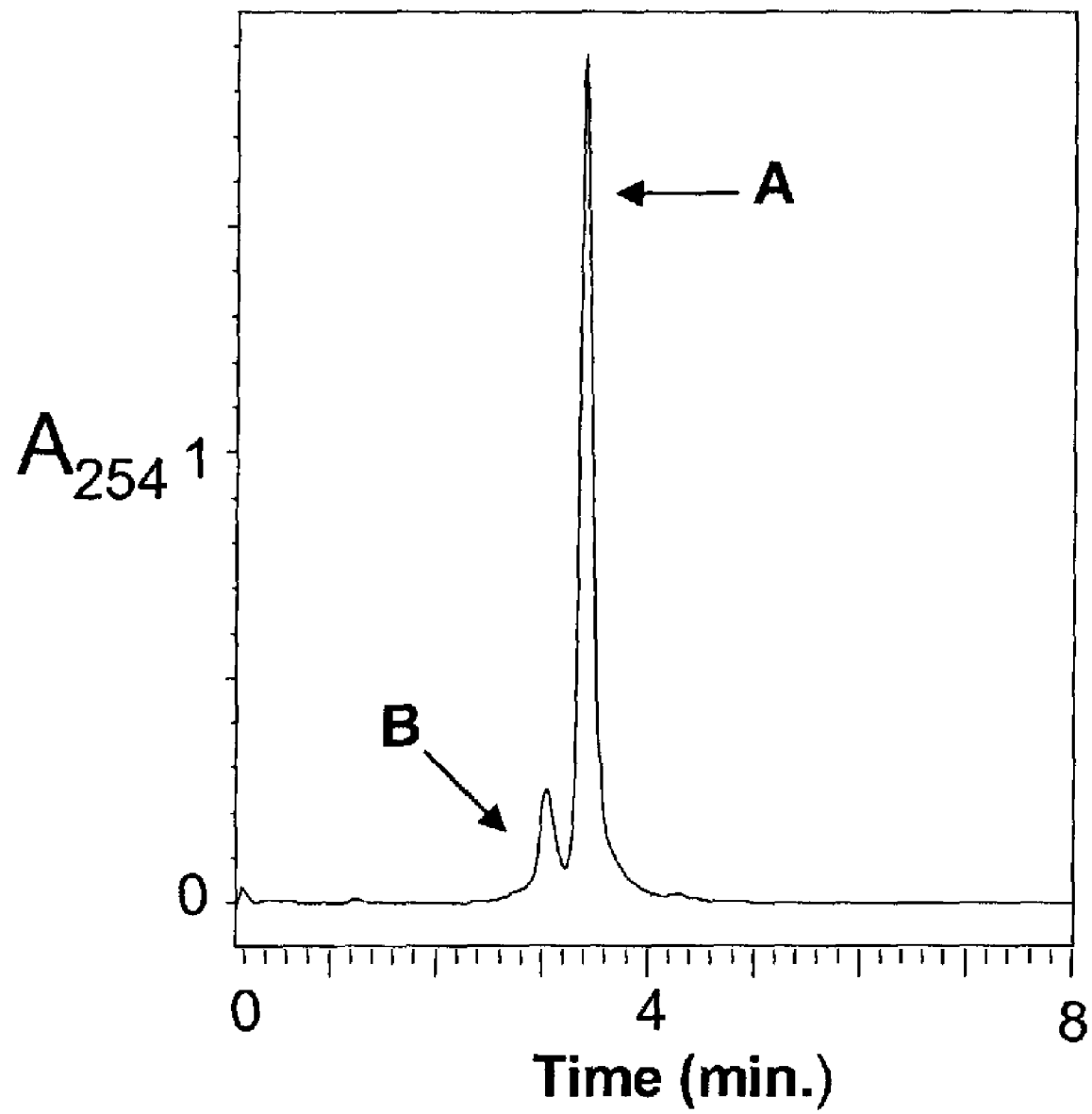
FIG. 2 illustrates a reversed-phase chromatogram of labeled 5'-β-actin-mdT(Ru(bpy)$_2$(mcbpy)) (arrow A) and unlabeled (arrow B).

5'-ApoB-mdT(Ru(bpy)$_2$(mcbpy))-(CPG), 5'-T$_9$-mdT(Ru(bpy)$_2$(mcbpy))-(CPG), 5'-β-Actin-TT-mdT(Ru(bpy)$_2$(mcbpy))-(CPG), and 5'-β-Actin-mdT(Ru(bpy)$_2$(mcbpy))-(CPG) are exposed to ammonia at 60° C. to produce the corresponding solution phase luminescent metal ion complexes. A spectral profile of 5'-T$_9$-mdT(Ru(bpy)$_2$(mcbpy)) is shown in FIG. 1 with $\lambda_{ABSMAX}$=460 nm (arrow A) and $\lambda_{EMMAX}$=650 nm (arrow B). A reversed-phase chromatogram of crude 5'-β-actin-Ru(bpy)$_2$(mcbpy) is shown in FIG. 2 (arrow A).

Example 1.6

Preparation of the Nucleic Acid Luminescent Metal Ion Complexes Containing Ru(phen)$_2$(mcbpy)

Using the procedures outlined in Examples 1.1-1.4, the corresponding nucleic acid luminescent metal ion complexes containing Ru(phen)$_2$(mcbpy) are produced by using Ru(phen)$_2$Cl$_2$ in place of Ru(bpy)$_2$Cl$_2$ and carboxy(mcbpy) in place of 1-carboxy-8-methyl bipyridine. Ru(phen)$_2$Cl$_2$ was prepared from phenanthroline and RuCl$_3$. Ru(phen)$_2$(mcbpy)-T$_9$ showed nearly the same absorption and emission spectra as Ru(bpy)$_2$(mcbpy)-T$_9$.

Example 1.7

Preparation of a Nucleic Acid Probes Containing Multiple Luminescent Metal Ion Complexes 8 was loaded onto a Biosearch 8700 DNA synthesizer and subjected to successive round of standard oligonucleotide synthesis using amino modifier C6 dT. Ru(bpy)$_2$(mcbpy) was activated with TSTU and DIEA in DMF and agitated overnight to allow coupling to the mdT-amines. Reversed phase HPLC yielded the following compounds: 5'-T$_3$-mdT(Ru(bpy)$_2$(mcbpy))-T$_2$-mdT(Ru(bpy)$_2$(mcbpy))-(CPG); 5'-mdT(Ru(bpy)$_2$(mcbpy))-T$_2$-mdT(Ru(bpy)$_2$(mcbpy))-T$_2$-mdT(Ru(bpy)$_2$(mcbpy))-(CPG); 5'-β-Actin-mdT(Ru(bpy)$_2$(mcbpy))-mdT(Ru(bpy)$_2$(mcbpy))-(CPG); and 5'-β-Actin-T-mdT(Ru(bpy)$_2$(mcbpy))-mdT(Ru(bpy)$_2$(mcbpy))-(CPG).

Deprotection and cleavage with ammonia at 60° C. yields the corresponding solution phase oligonucleotides.

Alternatively, 8 is loaded onto a Biosearch 8700 DNA synthesizer and subjected to successive round of standard oligonucleotide synthesis using DMT-MMT-mdC PEG amidite at any position in the growing oligonucleotide chain. Treatment with mild acid (TCA) removes the DMT and MMT groups, exposing the reactive amino group for coupling to a carboxylic acid or active ester of a metal ion coordinating component on solid support. Subsequent treatment with ammonium hydroxide yields the corresponding solution phase nucleic acid probe.

Example 2

Example 2 illustrates a method of making the solid phase nucleic acid luminescent metal ion complex 5'-Ru(bpy)$_2$(mcbpy)-oligonucleotide

Example 2.1

Preparation of Ru(bpy)$_2$(mcbpy)

Equal molar amounts of Ru(bpy)$_2$Cl$_2$ and mcbpy were refluxed in ethanol/water (2/3, v/v) for 3 hours. The solvent was removed by rotoevaporation and no purification was performed.

Example 2.2

Preparation of 5'-Ru(bpy)$_2$(mcbpy)-oligonucleotide

CPG-oligonucleotide was coupled with mdC-DMT-MMT-amine amidite. The DMT and MMT groups are then fully removed. A reaction solution was prepared by dissolving 2.5 mg of Ru(bpy)$_2$(mcbpy) and 2.5 mg of BOP in 0.2 mL of DMF with 10 µL of n-methylmorpholine. The 5'amino-oligo-CPG was reacted with the solution using the two-syringe technique. After 4 or more hours at room temperature, the column is rinsed with acetonitrile and normal deprotection with ammonia at 60° C. and purification was preformed to obtain pure 5'-Ru(bpy)$_2$(mcbpy)-oligonucleotide.

Example 3

Example 3 illustrates methods of making nucleic acid dual labeled probes.

Example 3.1

Preparation of the Nucleic Acid Dual Labeled Probe 5'(Squaraine)-ApoB-mdT(Ru(bpy)$_2$(mcbpy)

A crude sample of Squaraine-acid (see structure A below) was coupled to the 5'-NH$_2$-mdC-ApoB-mdT(Ru(bpy)$_2$(mcbpy))-(CPG) via syringe coupling in DMF with BOP and n-methylmorpholine. The resulting solid phase oligonucleotide was cleaved with ammonia at 60° C. Analytical AX HPLC of the crude solution showed that the major peak was the desired product (ca. 50% yield). The probe was purified by reverse-phase HPLC.

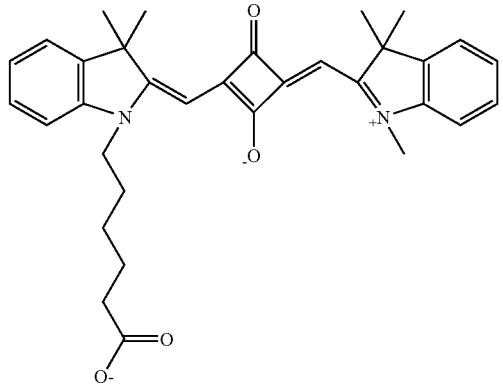

Structure A

Example 3.2

Preparation of Nucleic Acid Dual Labeled Probes Containing Black Hole Quenchers

A 5'-BHQ2-phosphoramidite was added to the 5' end of solid phase nucleic acid metal ion complexes to yield the following dual labeled nucleic acid probes: 5'-BHQ2-β-Actin-mdT(Ru(bpy)$_2$(mcbpy)); 5'-BHQ2-β-Actin-mdT(Ru(bpy)$_2$(mcbpy))-mdT(Ru(bpy)$_2$(mcbpy)); 5'-BHQ2-β-Actin-T-mdT(Ru(bpy)$_2$(mcbpy))-mdT(Ru(bpy)$_2$(mcbpy)).

Example 4

Example 4 illustrates various assay using dual labeled nucleic acid probes produce in examples 1-4.

Example 4.1

Hybridization Assay Using 5'(Squaraine)-ApoB-mdT(Ru(bpy)$_2$(mcbpy)

The absorption and emission spectra of the 5'(Squaraine)-ApoB-mdT(Ru(bpy)$_2$(mcbpy) probe were measured in buffer solution. A five-fold excess of complement was added and allowed to hybridize for 5 minutes (or until the fluorescence intensity became constant). The absorption and emission spectra of the probe and complement were then measured. The signal/background ratio was calculated by dividing the emission intensity of the probe and complement by the emission intensity of the probe.

Figure 3:
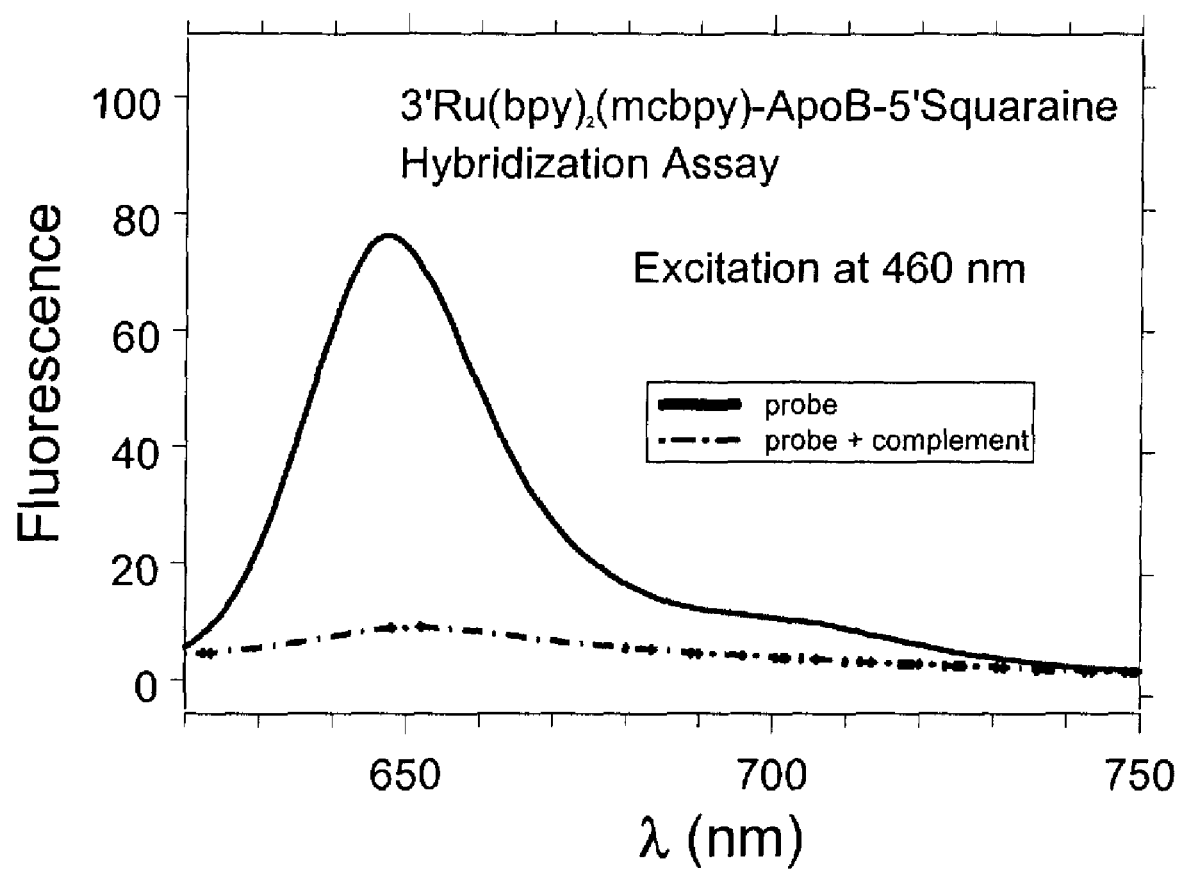
FIG. 3 illustrates a hybridization assay showing the 5'(Squaraine)-ApoB-mdT(Ru(bpy)$_2$(mcbpy) probe hybridized to a complementary oligonucleotide sequence (arrow A) and unbound (arrow B).
Figure 4:
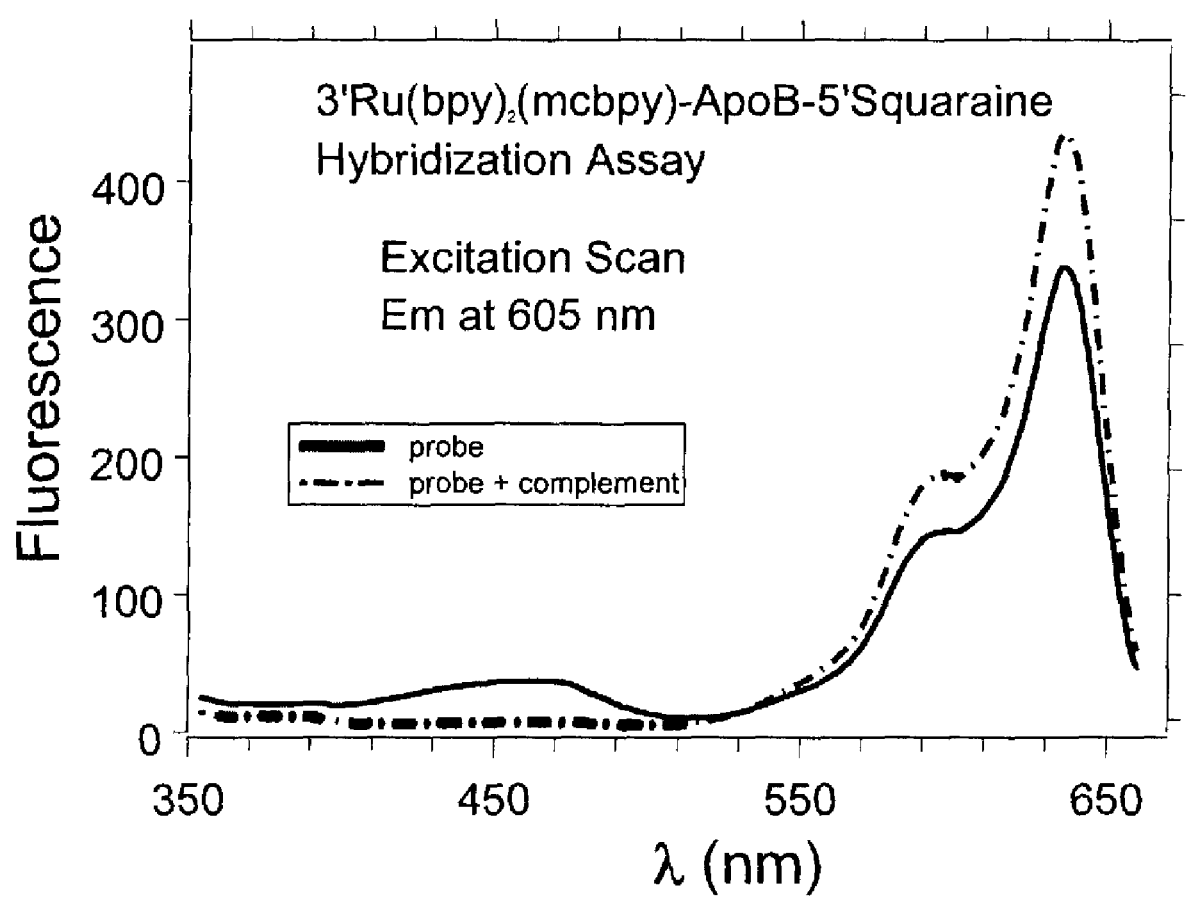
FIG. 4 illustrates an excitation spectra of the 5'(Squaraine)-ApoB-mdT(Ru(bpy)$_2$(mcbpy) probe hybridized to a complementary oligonucleotide sequence (arrow A) and unbound (arrow B).

Comparison of fluorescence and fluorescence excitation scans before and after the addition of complement show that the squaraine chromophore quenches the Ru(bpy)$_2$(mcbpy). See FIG. 3 and FIG. 4. The squaraine dye has absorption maximum at 635 nm and fluorescence maximum at 645 nm. Excitation of the Ru(bpy)$_3$ at 460 nm results in squaraine emission when the probe is unhybridized (arrow A), but when the complementary oligo sequence is added, the squaraine emission is dramatically decreased (arrow B). This shows that when hybridization separates the Ru(bpy)$_3$ and squaraine dyes, energy transfer from Ru(bpy)$_3$ to the squaraine is diminished. The excitation spectrum monitors the intensity of the squaraine emission as the excitation wavelength is scanned. When the probe is hybridized, 450 nm excitation of the Ru(bpy)$_2$(mcbpy) chromophore does not lead to squaraine fluorescence demonstrating that there is inefficient energy transfer. But when the probe is unhybridized, 450 nm excitation leads to squaraine emission.

Example 4.2

Emission Intensity Assay Using Nucleic Acid Probes Containing Multiple Luminescent Metal Ion Complexes Three nucleic acid probes containing multiple luminescent metal ion complexes were prepared as disclosed in Example 1. The emission intensity of the three nucleic acid probes were compared to determine whether the Ru(bpy)$_2$(mcbpy) self quenches. The results are shown in Table 2.

TABLE 2

| Sample | Sequence | Emission intensity of undigested/digested |
|---|---|---|
| Ru1 | 5'-T$_6$-mdT(Ru(bpy)$_2$(mcbpy)) | 0.83 |
| Ru2 | 5'-T$_3$-mdT(Ru(bpy)$_2$(mcbpy))-T$_2$-mdT(Ru(bpy)$_2$(mcbpy)) | 0.80 |
| Ru3 | 5'-mdT(Ru(bpy)$_2$(mcbpy))-T$_2$-mdT(Ru(bpy)$_2$(mcbpy))-T$_2$-mdT(Ru(bpy)$_2$(mcbpy)) | 0.80 |

As shown in Table 2, the three samples experienced a similar effect which indicates that the neighboring Ru(bpy)$_2$(mcbpy) luminescent complexes are not self-quenching.

Example 4.3

Digestion and Hybridization Assay Using Nucleic Acid Probes Containing Multiple Luminescent Metal Ion Complexes Three dual labeled probes containing a single or multiple luminescent metal ion complexes were prepared as disclosed in Examples 1 and 3. Table 3 shows the emission intensity of the three probes under different conditions. The probes were dissolved in 10 mM tris, 1 mM CaCl$_2$ buffer and the emission intensity was measured for each probe alone, after addition of micrococcal nuclease, and after the complementary oligo sequence was added.

TABLE 3

| Sample | Probe Alone | Digested Probe | Hybridized Probe |
|---|---|---|---|
| Ru$_1$/BHQ2 | 1.0 | 18 | 18 |
| Ru$_2$/BHQ2 | 3.7 | 31 | 41 |
| Ru$_3$/BHQ2 | 5.1 | 54 | 63 |

In Table 3, Ru$_1$/BHQ2 is 5'-BHQ2-β-Actin-mdT(Ru(bpy)$_2$(mcbpy)); Ru$_2$/BHQ2 is 5'-BHQ2-β-Actin-mdT(Ru(bpy)$_2$(mcbpy))-mdT(Ru(bpy)$_2$(mcbpy)); and Ru$_3$/BHQ2 is 5'-BHQ2-β-Actin-T-mdT(Ru(bpy)$_2$(mcbpy))-mdT(Ru(bpy)$_2$(mcbpy)).

As shown in Table 3, a single 5'BHQ-2 label can efficiently quench 1, 2 or 3 Ru(bpy)$_2$(mcbpy) labels.

Example 5

Example 5 illustrates the utility of a dual labeled probe as a molecular beacon.

Figure 5:
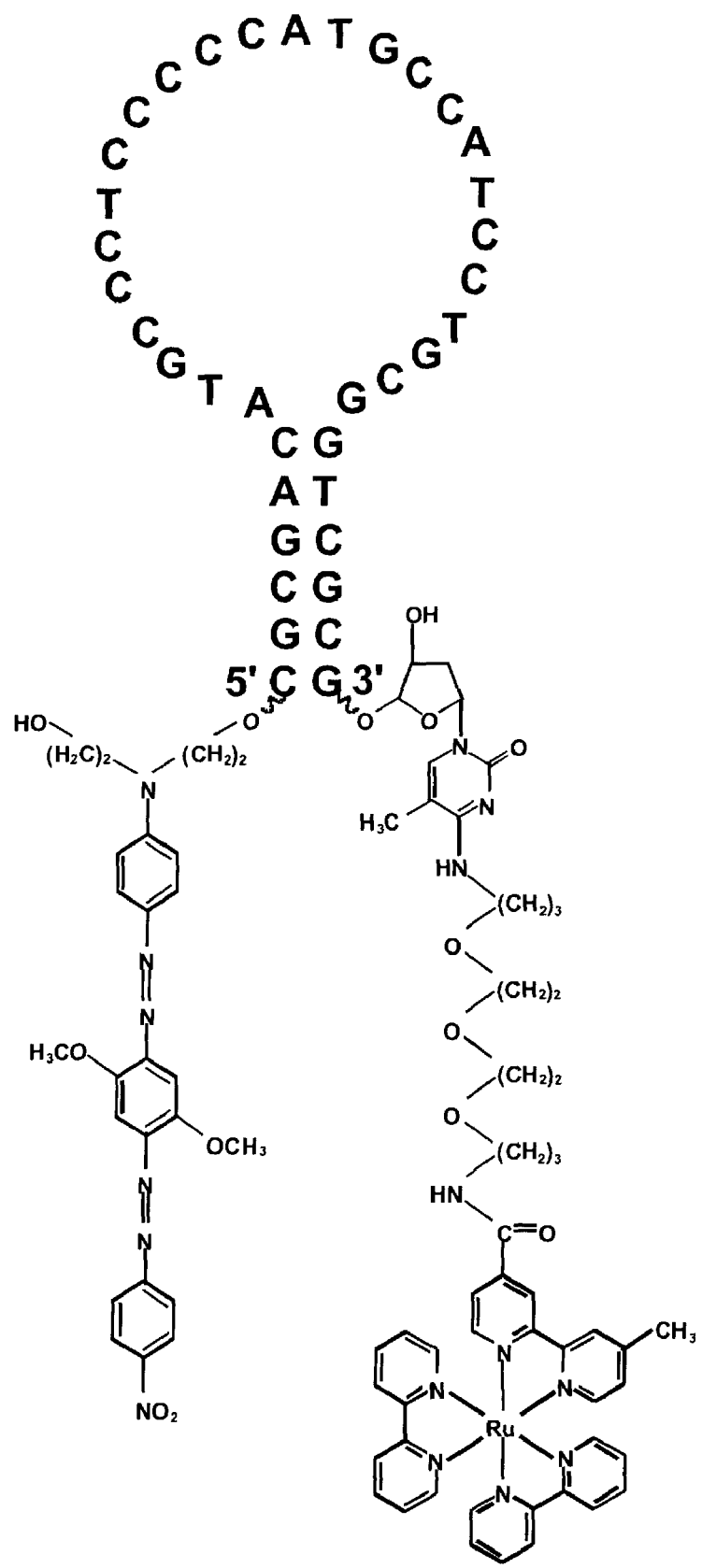
FIG. 5 illustrates dual labeled probe containing a stem loop structure (molecular beacon).

A dual labeled probe was synthesize according to the methods of example 1 with the following sequence: 5'-BHQ2-CGC-GAC-ATG-CCC-TCC-CCC-ATG-CCA-TCC-TGC-CCT-CGC-GmdT(Ru(bpy)$_2$(mcbpy)). The dual labeled robe is capable of forming a stem loop structure as shown in FIG. 5.

Figure 6:
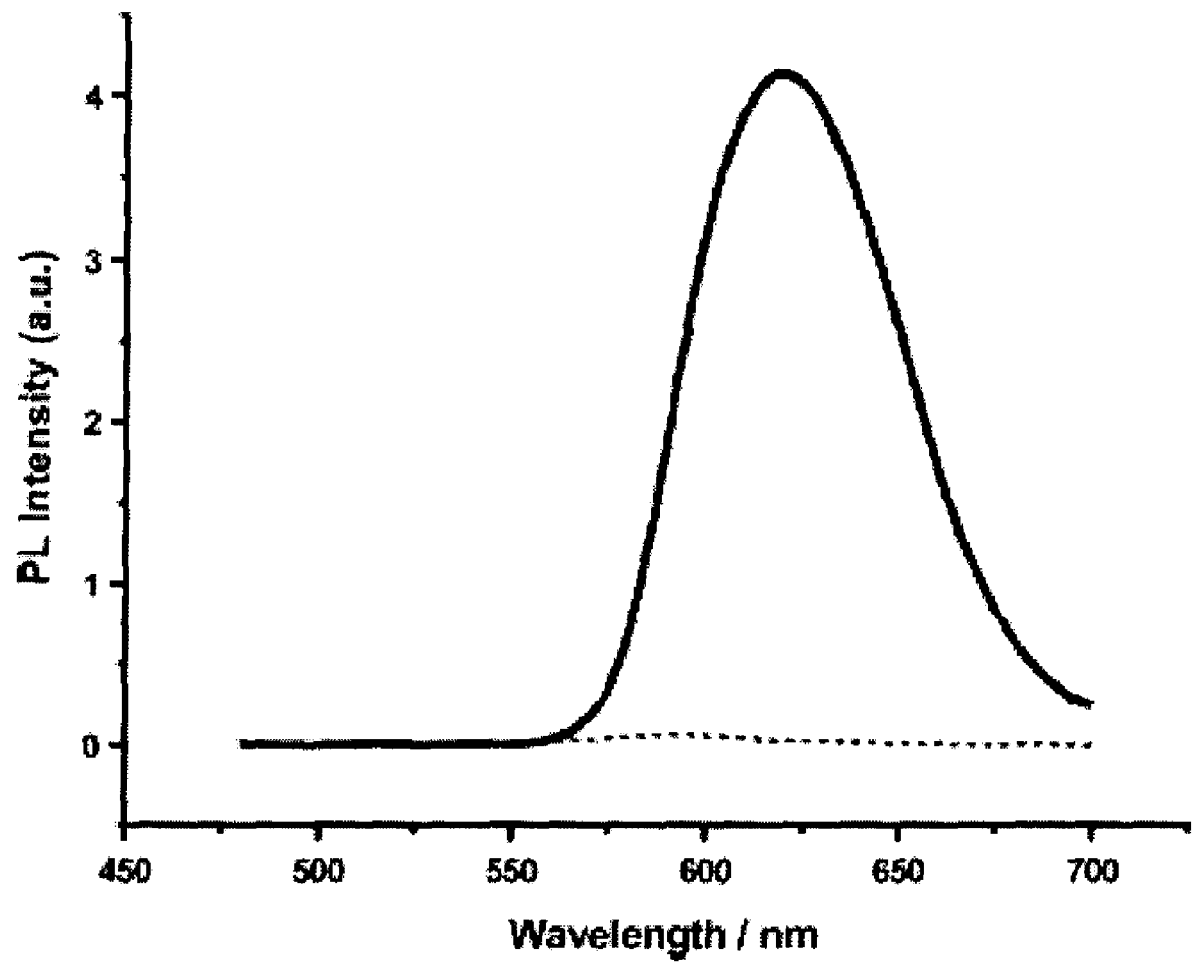
FIG. 6 illustrates the emission of a dual labeled probe containing a stem loop structure which has been excited by 450 nm light.
Figure 7:
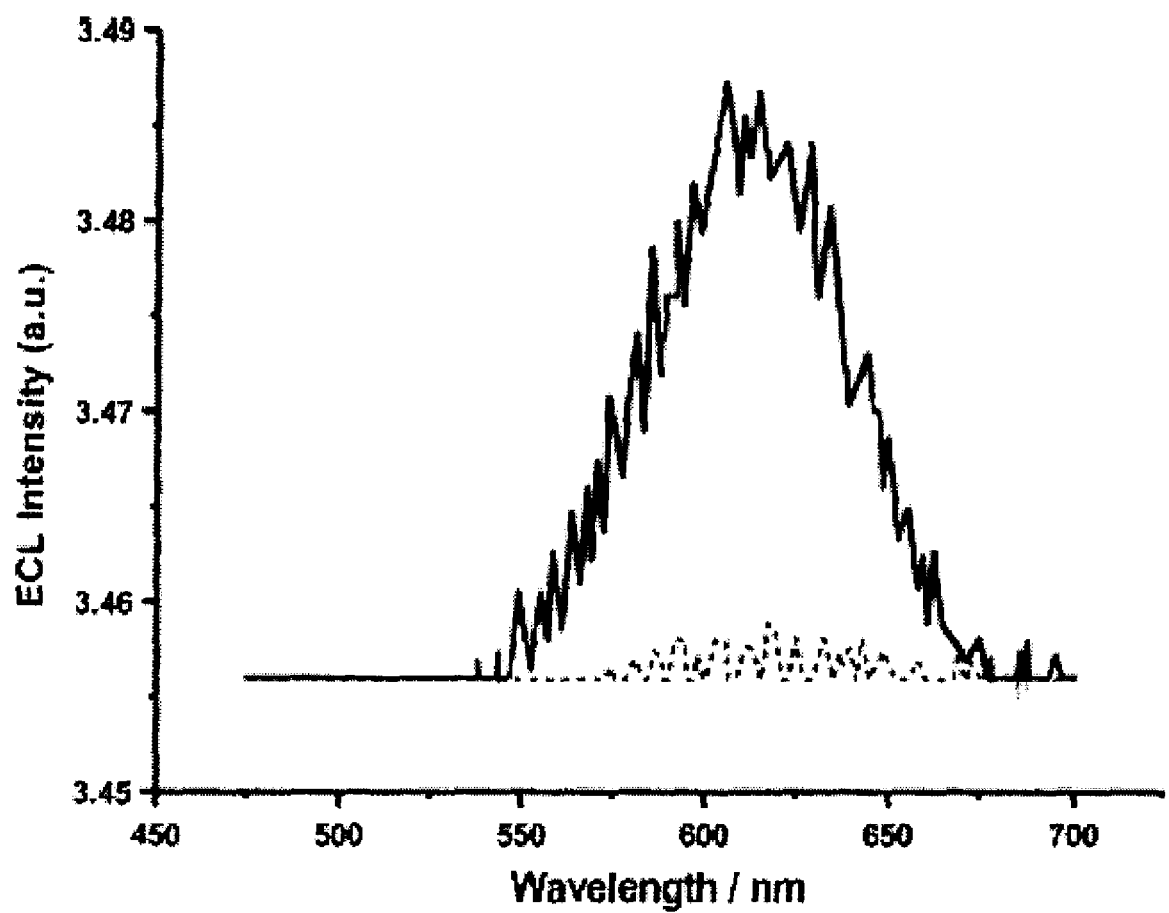
FIG. 7 illustrates emission of dual labeled probe containing a stem loop structure which has been excited electrochemically.

FIG. 6 and FIG. 7 show that dual labeled probes can be excited with light as well as electrochemically, respectively. In addition, the intensity was found to increase dramatically upon hybridization of the detector oligonucleotide (CGC-GAC-ATG-CCC-TCC-CCC-ATG-CCA-TCC-TGC-CCT-CGC) with the complementary sequence.

Example 6

Example 6 illustrates an exemplary coupling of Ru(bpy)$_2$(mcbpy) to peptide amines.

Ru(bpy)$_2$(mcbpy) is activated with 15 mg of TSTU and 12 μL DIEA in 0.3 mL of DMF and contacted with the appropriate peptide containing a reactive amine. The Ru(bpy)$_2$(mcbpy) is then allowed to covalently bond to the peptide reactive amine.

Alternatively, Ru(bpy)$_2$(mcbpy) is activated with BOP and n-methylmorpholine in DMF.

---

What is claimed is:

1. A metal ion coordinating component of a luminescent metal ion complex comprising:
   (i) a solid support covalently bonded to a non-nucleic acid spacer;
   (ii) a nucleobase covalently bonded to said non-nucleic acid spacer, wherein said nucleobase comprises a nitrogenous base;
   (iii) a linker covalently bonded to said nitrogenous base; and
   (iv) a metal ion coordinating moiety covalently bonded to said linker to form said metal ion coordinating component.

2. The metal ion coordinating component of claim 1, wherein said first nucleobase is covalently bonded to an oligonucleotide.

3. The metal ion coordinating component of claim 2, wherein said oligonucleotide comprises from 1 to 5 additional metal ion coordinating moieties covalently bound to said oligonucleotide.

4. The metal ion coordinating component of claim 1, wherein said metal ion coordinating moiety is a bidentate metal ion coordinating moiety.

5. The metal ion coordinating component of claim 1 wherein said linker has the formula:

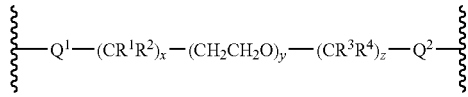

wherein,
$R^1$, $R^2$, $R^3$, and $R^4$ are individually selected from the group consisting of hydrogen, halogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and $OR^5$, wherein $R^5$ is selected from hydrogen and substituted or unsubstituted alkyl;
$Q^1$ and $Q^2$ are individually selected from the group consisting of a bond, substituted or unsubstituted alkyl, and substituted or unsubstituted heteroalkyl;
x and z are individually selected from the integers 0 to 10;
y is selected from the integers 1 to 10.

6. The metal ion coordinating component of claim 4, wherein said bidentate metal ion coordinating moiety is selected from the group consisting of substituted or unsubstituted bipyridyl, substituted or unsubstituted phenanthroline, substituted or unsubstituted 2,4 pentanediene, substituted or unsubstituted hydroxamate, substituted or unsubstituted terpyridine, substituted or unsubstituted dipyridophenazine, and substituted or unsubstituted acetylacetonate.

7. The metal ion coordinating component of claim 4, wherein said nitrogenous base is selected from the group consisting of guanine, thymine, cytosine, adenine, and uracil.

8. The metal ion coordinating component of claim 4, wherein said solid support is controlled pore glass.

9. The metal ion coordinating component of claim 4, wherein said bidentate metal ion coordinating moiety has the formula:

63

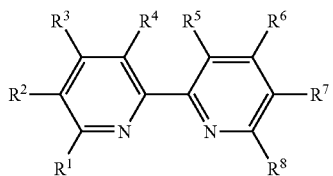

wherein,
- $R^1$, $R^2$, $R^3$, $R^4$, $R^5$, $R^6$, $R^7$, and $R^8$ are independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^A$, $NR^BR^C$, $NR^DOR^E$, $SR^F$, and $SO_2R^G$ wherein $R^4$ and $R^5$ are optionally joined together with the atoms to which they are attached to form a 3 to 8 membered ring,
- $R^A$, $R^B$, $R^C$, $R^D$, $R^E$, $R^F$, and $R^G$ are independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and
- one of $R^1$, $R^2$, $R^3$, $R^4$, $R^5$, $R^6$, $R^7$, and $R^8$ is attached to said linker.

10. The metal ion coordinating component of claim 2, further comprising a quencher of excited state energy, wherein said quencher is covalently attached to said oligonucleotide.

11. The metal ion coordinating component of claim 4, further comprising a metal ion, a second metal ion coordinating component, and a third metal ion coordinating component, wherein said metal ion coordinating component, said second metal ion coordinating component and said third metal ion coordinating component are coordinated to said metal ion to form said luminescent metal ion complex.

12. The metal ion coordinating component of claim 11, wherein said metal ion coordinating component comprises a first bidentate metal ion coordinating moiety, said second metal ion coordinating component comprises a second bidentate metal ion coordinating moiety, and said third metal ion coordinating component comprises a third bidentate metal ion coordinating moiety.

13. The metal ion coordinating component of claim 12, wherein said first bidentate metal ion coordinating moiety, said second bidentate metal ion coordinating moiety, and said third bidentate metal ion coordinating moiety are individually selected from the group consisting of substituted or unsubstituted bipyridyl, substituted or unsubstituted phenanthroline, substituted or unsubstituted 2,4 pentanediene, substituted or unsubstituted hydroxamate, substituted or unsubstituted terpyridine, and substituted or unsubstituted acetylacetonate.

14. The metal ion coordinating component of claim 11, wherein said metal ion is selected from the group consisting of ruthenium, osmium, and rhenium.

15. The metal ion coordinating component of claim 11, further comprising a quencher of excited state energy.

16. The metal ion coordinating component of claim 5, wherein
- x and z are individually selected from the integers 0 to 5; and
- y is selected from the integers 1 to 5.

64

17. The metal ion coordinating component of claim 1, wherein said linker has the formula:

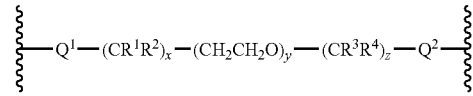

wherein,
- $R^1$, $R^2$, $R^3$, and $R^4$ are individually selected from the group consisting of hydrogen, halogen, —OH, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and $OR^5$, wherein
  - $R^5$ is selected from hydrogen and substituted or unsubstituted alkyl;
- $Q^1$ and $Q^2$ are individually selected from the group consisting of a bond, —NH—, —C(O)—, —C(O)NH—, —C(O)O—, —O—, —S—, —S—S—, and —N═N—;
- x and z are individually selected from the integers 0 to 10;
- y is selected from the integers 1 to 10.

18. The metal ion coordinating component of claim 17, wherein
- x and z are individually selected from the integers 0 to 5; and
- y is selected from the integers 1 to 5.

19. The metal ion coordinating component of claim 17, wherein $Q^1$ is —NH— and $Q^2$ is —C(O)NH—.

20. The metal ion coordinating component of claim 17, wherein $R^1$, $R^2$, $R^3$, and $R^4$ are hydrogen.

21. The metal ion coordinating component of claim 1, having the formula:

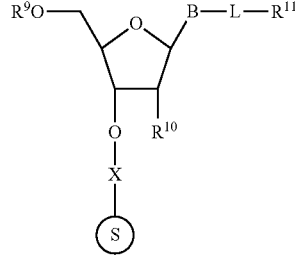

wherein
- $R^9$ is a member selected from hydrogen, substituted or unsubstituted alkyl, substituted or unsubstituted aryl, substituted or unsubstituted heteroaryl, substituted or unsubstituted heterocycloalkyl, a nucleobase and an oligonucleotide;
- $R^{10}$ is a member selected from hydrogen, substituted or unsubstituted alkyl, substituted or unsubstituted aryl, substituted or unsubstituted heteroaryl, substituted or unsubstituted heterocycloalkyl, halogen, and $OR^{12}$ wherein $R^{12}$ is a member selected from hydrogen, substituted or unsubstituted alkyl, and substituted or unsubstituted heteroalkyl;
- $R^{11}$ is said metal ion coordinating moiety;
- X is said non-nucleic acid spacer;
- B is said nitrogenous base;
- L is said linker; and
- S is said solid support.

22. The metal ion coordinating component of claim 21, further comprising a metal ion, a second metal ion coordinating component, and a third metal ion coordinating component, wherein said metal ion coordinating component, said second metal ion coordinating component and said third metal ion coordinating component are coordinated to said metal ion to form said luminescent metal ion complex.

23. The metal ion coordinating component of claim 21, having the formula:

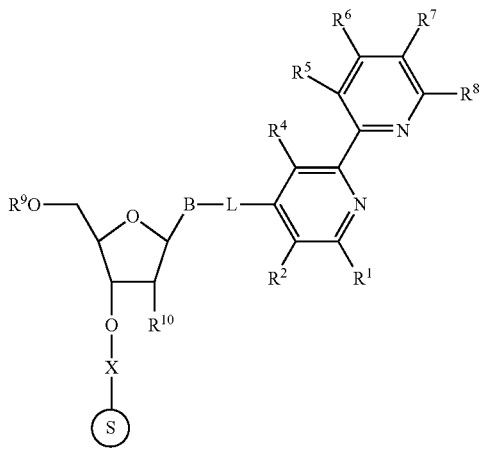

wherein
$R^1$, $R^2$, $R^3$, $R^4$, $R^5$, $R^6$, $R^7$, and $R^8$ are independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^A$, $NR^B R^C$, $NR^D OR^E$, $SR^F$, and $SO_2 R^G$
wherein
$R^4$ and $R^5$ are optionally joined together with the atoms to which they are attached to form a 3 to 8 membered ring; and
$R^A$, $R^B$, $R^C$, $R^D$, $R^E$, $R^F$, and $R^G$ are independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

24. The metal ion coordinating component of claim 23, further comprising a metal ion, a second metal ion coordinating component, and a third metal ion coordinating component, wherein said metal ion coordinating component, said second metal ion coordinating component and said third metal ion coordinating component are coordinated to said metal ion to form said luminescent metal ion complex.

25. The metal ion coordinating component of claim 23, having the formula:

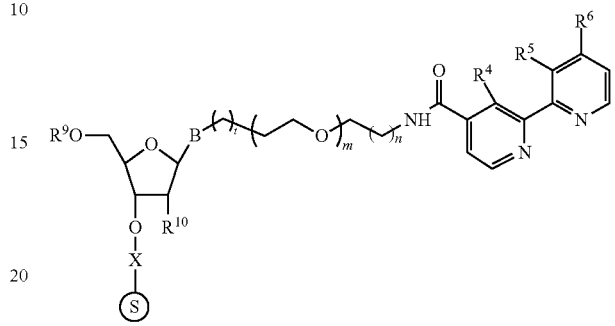

wherein
t and n are independently selected from the integers 0 to 10; and
m is selected from the integers 1 to 10.

26. The metal ion coordinating component of claim 25, further comprising a metal ion, a second metal ion coordinating component, and a third metal ion coordinating component, wherein said metal ion coordinating component, said second metal ion coordinating component and said third metal ion coordinating component are coordinated to said metal ion to form said luminescent metal ion complex.

27. The metal ion coordinating component of claim 25, wherein
t and n are independently selected from the integers 0 to 5; and
m is selected from the integers 1 to 5.

28. The metal ion coordinating component of claim 27, having the formula:

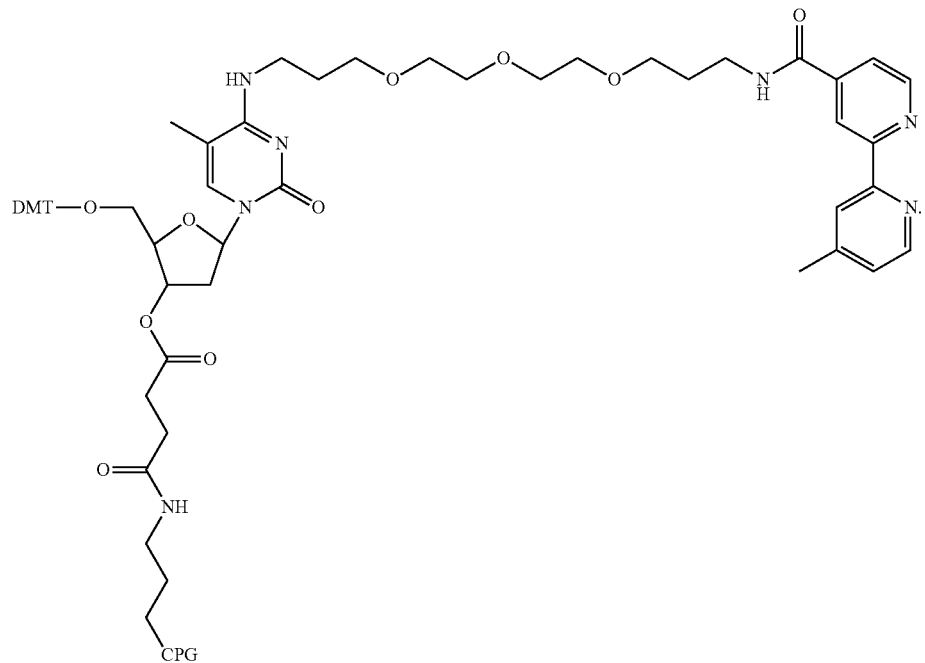

29. The metal ion coordinating component of claim 28, further comprising a metal ion, a second metal ion coordinating component, and a third metal ion coordinating component, wherein said metal ion coordinating component, said second metal ion coordinating component and said third metal ion coordinating component are coordinated to said metal ion to form said luminescent metal ion complex.

30. The metal ion coordinating component of claim 29, wherein said metal ion is ruthenium; and
said second metal ion coordinating component and said third metal ion coordinating component are each substituted or unsubstituted bipyridyl.

31. The metal ion coordinating component of claim 30, wherein
said metal ion is $Ru^{2+}$; and
said second metal ion coordinating component and said third metal ion coordinating component are each 2,2'-bipyridine.

32. A nucleic acid luminescent metal ion complex having the formula:

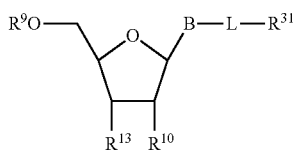

wherein
$R^9$ is an oligonucleotide;
$R^{10}$ is a member selected from hydrogen, substituted or unsubstituted alkyl, substituted or unsubstituted aryl, substituted or unsubstituted heteroaryl, substituted or unsubstituted heterocycloalkyl, halogen, and $OR^{12}$
wherein $R^{12}$ is a member selected from hydrogen, substituted or unsubstituted alkyl, and substituted or unsubstituted heteroalkyl;
$R^{13}$ is OH;
B is a nitrogenous base;
L is a linker; and
$R^{31}$ is a luminescent metal ion complex.

33. The nucleic acid luminescent metal ion complex of claim 32, wherein $R^{10}$ is hydrogen.

34. The nucleic acid luminescent metal ion complex of claim 32, having the formula:

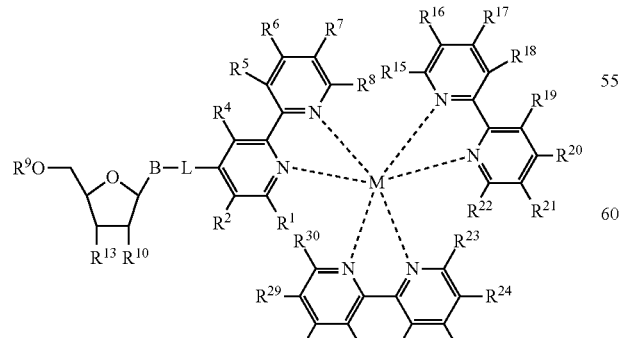

wherein $R^1$, $R^2$, $R^3$, $R^4$, $R^5$, $R^6$, $R^7$, and $R^8$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^A$, $NR^BR^C$, $NR^DOR^E$, $SR^F$, and $SO_2R^G$ wherein $R^4$ and $R^5$ are optionally joined together with the atoms to which they are attached to form a 3 to 8 membered ring; and $R^A$, $R^B$, $R^C$, $R^D$, $R^E$, $R^F$, and $R^G$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^A$, $NR^BR^C$, $NR^DOR^E$, $SR^F$, and $SO_2R^G$ wherein $R^{18}$ and $R^{19}$ are optionally joined together with the atoms to which they are attached to form a 3 to 8 membered ring; and $R^{26}$ and $R^{27}$ are optionally joined together with the atoms to which they are attached to from a 3 to 8 membered ring; and M is a metal ion selected from a lanthanide metal and a transition metal.

35. The nucleic acid luminescent metal ion complex of claim 34, wherein said metal ion is selected from ruthenium, osmium, and rhenium.

36. The nucleic acid luminescent metal ion complex of claim 34, having the formula:

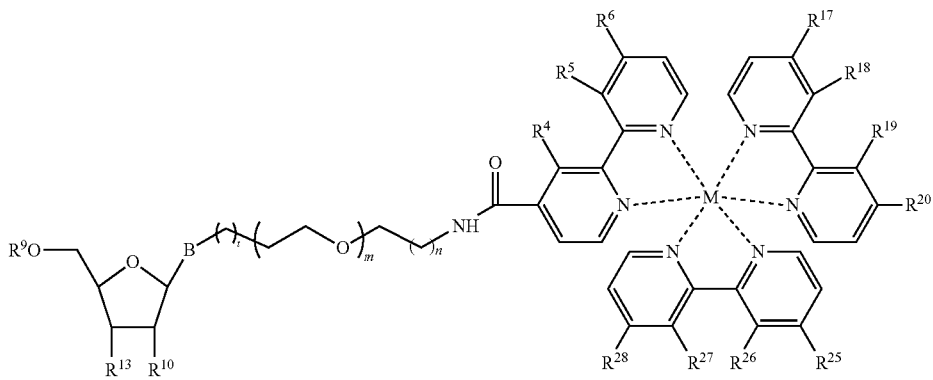
wherein
t and n are independently selected from the integers 0 to 10; and
m is selected from the integers 1 to 10.
37. The nucleic acid luminescent metal ion complex of claim 36, wherein
t and n are independently selected from the integers 0 to 5; and
m is selected from the integers 1 to 5.
38. The nucleic acid luminescent metal ion complex of claim 37, having the formula:
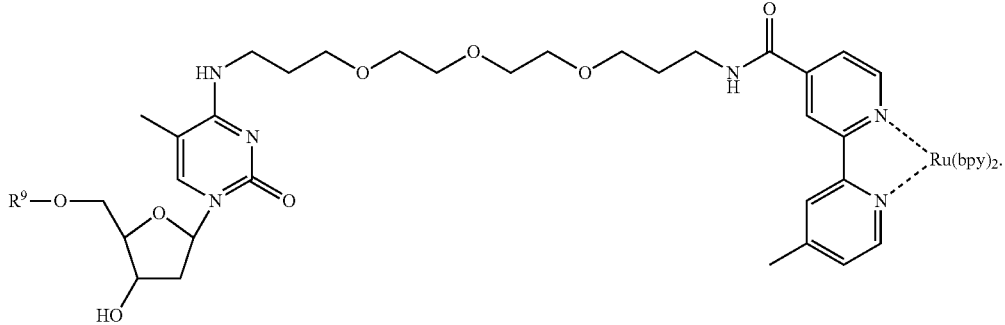
* * * * *

SEQUENCE LISTING

```
<160> NUMBER OF SEQ ID NOS: 5

<210> SEQ ID NO 1
<211> LENGTH: 26
<212> TYPE: DNA
<213> ORGANISM: Artificial sequence
<220> FEATURE:
<223> OTHER INFORMATION: Apo B sequence

<400> SEQUENCE: 1
cgagaatcac cctgccagac ttccgt                                           26

<210> SEQ ID NO 2
<211> LENGTH: 25
<212> TYPE: DNA
<213> ORGANISM: Artificial sequence
<220> FEATURE:
<223> OTHER INFORMATION: Beta-action sequence

<400> SEQUENCE: 2
```

```
atgccctccc ccatgccatc ctgcg                                       25

<210> SEQ ID NO 3
<211> LENGTH: 37
<212> TYPE: DNA
<213> ORGANISM: Artificial sequence
<220> FEATURE:
<223> OTHER INFORMATION: Probe

<400> SEQUENCE: 3
cgcgacatgc cctcccccat gccatcctgc cctcgcg                          37

<210> SEQ ID NO 4
<211> LENGTH: 36
<212> TYPE: DNA
<213> ORGANISM: Artificial sequence
<220> FEATURE:
<223> OTHER INFORMATION: Detector oligonucleotide

<400> SEQUENCE: 4
cgcgacatgc cctcccccat gccatcctgc cctcgc                           36

<210> SEQ ID NO 5
<211> LENGTH: 37
<212> TYPE: DNA
<213> ORGANISM: Artificial sequence
<220> FEATURE:
<223> OTHER INFORMATION: Stem loop sturcture of figure 5

<400> SEQUENCE: 5
cgcgacatgc cctcccccat gccatcctgc ggtcgcg                          37
```